US008846309B2

(12) United States Patent
Shou et al.

(10) Patent No.: US 8,846,309 B2
(45) Date of Patent: Sep. 30, 2014

(54) METHODS FOR DETECTING LP-PLA2 ACTIVITY AND INHIBITION OF LP-PLA2 ACTIVITY

(75) Inventors: Yaping Shou, Research Triangle Park, NC (US); Yin-Fai Siu, Research Triangle Park, NC (US); George T. Walker, Research Triangle Park, NC (US)

(73) Assignee: Glaxo Group Limited, Brentford, Middlesex (GB)

( * ) Notice: Subject to any disclaimer, the term of this patent is extended or adjusted under 35 U.S.C. 154(b) by 405 days.

(21) Appl. No.: 12/817,677

(22) Filed: Jun. 17, 2010

(65) Prior Publication Data

US 2010/0256919 A1 Oct. 7, 2010

Related U.S. Application Data

(63) Continuation of application No. 11/106,239, filed on Apr. 14, 2005, now Pat. No. 7,741,020.

(60) Provisional application No. 60/563,078, filed on Apr. 16, 2004.

(51) Int. Cl.
*C12Q 1/00* (2006.01)
*C12Q 1/61* (2006.01)
*C12Q 1/34* (2006.01)
*C12Q 1/44* (2006.01)

(52) U.S. Cl.
CPC ............ *C12Q 1/61* (2013.01); *G01N 2333/918* (2013.01); *C12Q 2334/10* (2013.01); *C12Q 1/34* (2013.01); *C12Q 1/44* (2013.01)
USPC .......................................................... 435/4

(58) Field of Classification Search
USPC .......................................................... 435/4
See application file for complete search history.

(56) References Cited

U.S. PATENT DOCUMENTS

| 5,091,527 A | 2/1992 | Junius et al. |
| 5,532,152 A | 7/1996 | Cousens et al. |
| 5,605,801 A | 2/1997 | Cousens et al. |
| 5,641,669 A | 6/1997 | Cousens et al. |
| 5,656,431 A | 8/1997 | Cousens et al. |
| 5,698,403 A | 12/1997 | Cousens et al. |
| 5,847,088 A | 12/1998 | Cousens et al. |
| 5,977,308 A | 11/1999 | Cousens et al. |
| 5,981,252 A | 11/1999 | MacPhee et al. |
| 6,177,257 B1 | 1/2001 | MacPhee et al. |
| 6,203,790 B1 | 3/2001 | Cousens et al. |
| 7,052,862 B2 | 5/2006 | MacPhee et al. |
| 7,217,535 B2 | 5/2007 | MacPhee et al. |
| 7,301,043 B2 | 11/2007 | Deigner et al. |
| 7,416,853 B2 | 8/2008 | MacPhee et al. |
| 7,531,316 B2 | 5/2009 | Hu et al. |
| 7,741,020 B2 | 6/2010 | Shou et al. |
| 8,088,886 B2 | 1/2012 | MacPhee et al. |
| 2002/0081271 A1 | 6/2002 | Martin et al. |
| 2002/0102231 A1 | 8/2002 | Dietsch et al. |
| 2003/0072747 A1 | 4/2003 | Cousens et al. |
| 2003/0148398 A1 | 8/2003 | McPhee et al. |
| 2005/0064532 A1 | 3/2005 | Deigner et al. |
| 2007/0166777 A1 | 7/2007 | Shou et al. |
| 2007/0281323 A1 | 12/2007 | Wolfert et al. |
| 2012/0045774 A1 | 2/2012 | MacPhee et al. |
| 2012/0276569 A1 | 11/2012 | Shou et al. |
| 2013/0236450 A1 | 9/2013 | Montaner et al. |

FOREIGN PATENT DOCUMENTS

| EP | 0658205 A1 | 6/1955 |
| EP | 816504 A2 | 1/1998 |
| EP | 0658205 B1 | 3/2000 |
| EP | 0673426 B1 | 6/2001 |
| EP | 1318154 A1 | 6/2003 |
| EP | 1735457 A3 | 12/2005 |
| EP | 1718967 A2 | 11/2006 |
| EP | 05779946.2-2401 | 7/2007 |
| EP | 2253702 | 11/2010 |
| EP | 2290094 A1 | 3/2011 |
| JP | 4346797 A | 12/1992 |
| JP | 06116279 A | 4/1994 |
| JP | 07059597 | 3/1995 |
| JP | 2002-179545 | 6/2002 |
| JP | 2002223794 A | 8/2002 |
| WO | WO 9509921 A1 | 4/1995 |
| WO | WO00/24910 A1 | 5/2000 |
| WO | WO00/32808 A1 | 5/2000 |
| WO | WO00/66567 A1 | 11/2000 |
| WO | WO01/60805 A1 | 8/2001 |
| WO | WO02/30904 A1 | 4/2002 |
| WO | WO02/30911 A1 | 4/2002 |
| WO | WO03/041712 A1 | 5/2003 |

(Continued)

OTHER PUBLICATIONS

Min J., et al., "Platelet Activating Factor Acetylhydrolases: Broad Substrate Specificity and Lipoprotein Binding does not Modulate the Catalytic Properties of the Plasma Enzyme," *Biochemistry* 40(15):4539-4549 (2001).
Kosaka T., et al., "Serum Platelet-Activating Factor Acetylhydrolase Activity in more than 3000 Healthy Japanese," *Clinica Chimica Acta*. 312(1-2):179-183, 2001.
Kosaka T, et al., "Spectrophotometric Assay for Serum Platelet-Activating Factor Acetylhydrolase Activity," *Clinica Chimica Acta* (2000) 296(1-2):151-161.
Koenig W, et al., "Lipoprotein-Associated Phospholipase $A_2$ Adds to Risk Prediction of Incident Coronary Events by C-Reactive Protein in Apparently Healthy Middle-Aged Men from the General Population" *Circulation* (Oct. 2004) 110(14):1903-1908.
Balafa O, et al., "Urine of Patients with Nephritic Syndrome Contains the Plasma Type of PAF-Acetylhydrolase Associated with Lipoproteins," *Nephron Physiology* (2004)97(3):45-52.

(Continued)

*Primary Examiner* — Bin Shen
(74) *Attorney, Agent, or Firm* — Loretta J. Sauermelch; Alan X. Scrivner

(57) ABSTRACT

This invention relates to methods for determining the activity of Lp-PLA2 in at least one sample from an animal. The invention also relates to methods for determining the inhibition of Lp-PLA2 activity in samples from animals that are administered an Lp-PLA2 inhibitor.

38 Claims, No Drawings

(56) References Cited

FOREIGN PATENT DOCUMENTS

| WO | WO03/086400 A1 | 10/2003 |
|---|---|---|
| WO | WO03/087088 A2 | 10/2003 |
| WO | WO2004/089184 A1 | 10/2004 |
| WO | WO2005/001416 A2 | 1/2005 |
| WO | WO2005/113797 | 4/2005 |
| WO | WO2005/074604 A2 | 8/2005 |
| WO | 1735457 A2 | 12/2005 |
| WO | WO2005/113797 A2 | 12/2005 |
| WO | WO2005/113797 A3 | 12/2005 |
| WO | WO2011/137419 A1 | 11/2011 |

OTHER PUBLICATIONS

Sarchielli P, et al., "Platelet-Activating Factor (PAF) in Internal Jugular Venous Blood of Migraine without Aura Patients Assessed During Migraine Attacks," *Cephalagia* (2004) 24(8):623-630.
Karkabounas A., et al., "Quantitative Fluorescence Determination of Phospholipase $A_2$ and PAF Acetylhydrolase in Biological Fluids using High Performance Liquid Chromatography," *Chemistry and Physics of Lipids* (Jun. 2004)130(1):69-70.
Brites F, et al., "Paraoxonase 1 and Platelet-Activating Factor Acetylhydrolase Activities in Patients with Low HDL-Cholesterol Levels with or without Primary Hypertriglyceridemia," *Archives of Medical Research* (May 2004)35(3):235-240.
Kujiraoka T, et al., "Altered Distribution of Plasma PAF-AH between HDLs and other Lipoproteins in Hyperlipidemia and Diabetes Mellitus," *Journal of Lipid Research* (Oct. 2003) 44(10):2006-14.
Ito T, et al., "Serum PAF-Acetylhydrolase (PAF-AH) in Hepatobiliary Disease," *Japanese Pharmacology and Therapeutics* (2002) 30/Suppl. 2.
Unno, N et al., "Single Nucleotide Polymorphism ($G^{994}$→T) in the Plasma Platelet-Activating Factor-Acetylhydrolase Gene is Associated with Graft Patency of Femoropopliteal Bypass," *Surgery* (2002) 132(1):66-71.
Dada, N, et al, "LP-PLA2: an emerging biomarker of coronary heart disease," *Expert Review of Molecular Diagnostics* (Jan. 2002) 2(1):17-22.
Ibe B, et al. "Platelet Activating Factor Acetylhydrolase Activity in Lamb Lungs is Up-Regulated in the Immediate Newborn Period," *Molecular Genetics and Metabolism* (Jan. 2000) 69(1):46-55.
Deigner H, et al., "Novel reversible, irreversible and fluorescent inhibitors of platelet-activating factor acetylhydrolase as mechanistic probes," *Atherosclerosis* (May 1999) 144(1):79-90.
Kitsiouli E, et al. "Differential Determination of Phospholipase A(2) ane PAF-Acetylhydrolase in Biological Fluids Using Fluorescent Substrates," *Journal of Lipid Research* (Dec. 1999) 40(12):2346-2356.
Hendrickson HS, et al., "Intramolecularly Quenched BODIPY-Labeled Phospholipids Analogs in Phospholipase $A_2$ and Platelet-Activating Factor Acetylhydrolase assays and in Vivo Fluorescence Imaging," *Analytical Biochemistry* (Dec. 1999) 276(1):27-35.
Akiyama M, et al., "Identification of a Major PAF Acetylhydrolase in Human Serus/Plasma as a 43 KDa Glycoprotein Containing about 9 kDa Asparagine-Conjugated Sugar Chain(s)," *Journal of Biochemistry* (May 1998) 123(5):786-789.
Servillo L, et al., "Simultaneous Determination of Lysophospholipids by High-performance Liquid Chromatography with Fluorescence Detection," *Journal of Chromatography* (1997) 689(B):281-286.
Patrick DA, et al., "Reduced PAF-Acetylhydrolase Activity is Associated with Postinjury Multiple Organ Failure,", *Shock* (Mar. 1997)7(3):170-174.
Tsukioka K, et al., "Increased Plasma Level of Platelet-Activating Factor (PAF) and Decreased Serum PAF Acetylhydrolase (PAFAH) Activity in Adults with Bronchial Asthma," *Journal of Investigational Allergology and Clinical Immunology* (1996)6(1):22-29.
Balestrieri C, et al., "Measurement of Platelet-Activating Factor Acetylhydrolase Activity by Quantitative High-Performance Liquid Chromatography Determination of Courmarin-Derivatized 1-0-alkyl-2-sn-lysoglyceryl-3-phosphorylcholine," *Analytical Biochemistry* (Jan. 1996)233(2):145-50.
Riehl TE and Stenson WF., "Platelet-activating factor acetylhydrolases in Caco-2 cells and epithelium of normal and ulcerative colitis patients," *Gastroenterology* (1995)109(6):1826-1834.
Masaki A, et al., "New Serum PAF acetylhydrolase detection method used with the Blotting Method and Beta of $_3$Hacetyl-PAF," *Proceedings of Japanese Conference on the Biochemistry of Lipids* (1994)36:43-46.
Hemmings R, et al., "Platelet-Activating Factor Acetylhydrolase Activity in Peritoneal Fluids of Women with Endometriosis," *Obstetrics and Gynecology* (Feb. 1993)81(2):276-279.
Masao M et al., "On Development of a Measurement Method of Serum PAF Acetylhydrolase Activity Using an Automatic Analyser, and the Clinical Significance of Serum PAF Acetylhydrolase Defect," *Proceedings of Japanese Conference on the Biochemistry of Lipids* (1992)34:305-308.
Stafforini D., et al., "Platelet-Activating Factor Acetylhyrolase in Human erythrocytes," *Methods in Enzymology* (1991)197:411-425.
Kirschbaum B, "Platelet Activating Factor Acetylhydrolase activity in the urine of patients with renal disease," *Clinical Chimica Acta* (Jun. 14, 1991)199(2):139-146.
Imaizumi T et al., "Activity of platelet-activating factor (PAF) acetylhydrolase in plasma from healthy habitual cigarette smokers" *Heart and Vessels* (1990)5(2):81-86.
Matsuzaki Masaharu, "Measurement Methods of Platelet Activating Factor (PAF) and PAF Acetylhydrolase (PAFAH) Activity," *SRL Hokan* (1989)13(3): 36-41.
Schindler PW, et al, "Fluorophore-labeled ether lipids: substrates for enzymes of the platelet-activating factor cycle in peritoneal polymorphonuclear leukocytes," *Analytical Biochemistry* (Nov. 1988) 174(2):477-84.
Miwa, M., et al, "Characterization of serum platelet-activating factor (PAF) acetylhydrolase. Correlation between deficiency of serum PAF acetylhydrolase and respiratory symptoms in asthmatic children." *Journal of Clinical Investigation* (Dec. 1988)82(6):1983-1991.
Masao Miwa, et al., "Serum platelet-activating factor (PAF) acetylhydrolase of children with bronchial asthma," *Japanese Journal of Inflammation* (1988)8(4):327-333.
Satoh Kei, et al, "Platelet-activating factor (PAF) acetylhydrolase and plasma lipoproteins: Relative distribution of the activity among lipoprotein classes," *Journal of Japan Atheroschlerosis Society* (1988)16(4):501-504.
Stafforini D, et al., "Human Plasma Platelet-Activating Factor Acetylhyrolase. Purification and Properties," *Journal of Biological Chemistry* (1987)262(9):4223-4230.
Kawamura Y, "A Simple Measurement of Plasma Platelet-Activating Factor (PAF) Acetylhydrolase, Normal Level Activity, and Distribution Among Lipoprotein Fractions," *Japanese Journal of Clincal Pathology* (Oct. 1987)35(10):1149-1153.
Pritchard PH, et al. "The Degradation of Platelet-Activating Factor in the Plasma of a Patient with Familial High Density Lipoprotein Deficiency (Tangier Disease)" *Blood* (1985) 66(6):1476-1478.
Caslake MJ, et al., "Lipoprotein-associated Phospholipase $A_2$ platelet-activating factor acetylhydrolase: a potential new risk factor for coronary artery disease," *Atherosclerosis* 150(2): 413-9, (Jun. 2000).
Z. Flegar-Mestric, et al., "Serum platelet-activating factor acetylhydriolase activity in patients with angiogrphically established cerebrovascular stenosis," *Clinical Chemistry and Laboratory Medicine, Proceesing of the IFFCC-FESCC European Congress, 15th Barcelona, Spain*: 369-372 (Jun. 1-5, 2003) (Publisher Monduzzi Editore, Bologna, Italy.
Akiyama, Masaki, A, et al., "Determination of Platelet-Activating Factor Acetylhydrolase Activity by Blotting, β-Radioluminescence, and Ultrahigh-Sensitivity Television Camera Detection" *Analytical Biochemistry* 21(2):295-299 (May 1994).
Karlan Research Products Corporation, Santa Rosa, CA, "Auto PAF-AH Serum (plasma) platelet-activating factor (PAF) acetylhydrolase assay—Instruction Manual" (2005).
Cayman Chemical, Ann Arbor, MI "PAF Acetylhydrolase Assay Kit" Catalog No. 760901.

(56) References Cited

OTHER PUBLICATIONS

DiaDexus Inc., "Enzyme Immunoassay for the Quantitative Determination of Lp-PLA$_2$ in Human Plasma and Serum" (Aug. 2005).
Stafforini D., et al., "Platelet-Activating Factor Acetylhyrolase," *The Journal of Biological Chemistry* (1997)272(29):17895-17898.
Zalewski and MacPhee, "Role of Lipoprotein-Associated Phospholipase A2 in Atheriosclerosis," *Arterioscler Thromb Vasc Biol.* 2005; 25:923-931.
Thirkettle, et al., *J. Antibiotics*, 53(7):664-669 (2000).
Thirkettle, *J. Antibiotics*, 53(7):733-735 (2000).
Boyd, et al., *Bioorg. Med. Chem. Lett.*, 10:395-398 (2000).
Boyd, et al., *Bioorg. Med. Chem. Lett.*, 10:2557-2561 (2000).
Tew, et al., *Biochem.*, 37:10087-10093 (1998).
Tew, et al., *Arteriosclerosis, Thrombosis Vasc. Biol.*, 16(4):591-599 (1996).
Stafforini D., et al. *The Journal of Biological Chemistry* (1997) 272(29):17895-17898.
Zalewski and MacPhee. *Arterioscler Thromb Vasc Biol.* (2005) 25:923-931.
JP 4346797A Japanese patent application (Dec. 2, 1992)—abstracts (Derwent Information Ltd; HCAPLUS/ACS on STN)—2 pages.
JP 3036883B2 Japanese Patent (Apr. 24, 2000)—Paterra® InstantMT® Machine Translation—13 pages.
JP 6116279A Japanese patent application (Apr. 26, 1994)—abstract (Derwent Information Ltd)—1 page.
JP 6116279A Japanese patent application (Apr. 26, 1994)—Paterra® InstantMT® Machine Translation—28 pages.
JP 7059597A Japanese patent application (Mar. 5, 1995)—abstracts (Derwent Information Ltd; HCAPLUS/ACS on STN)—2 pages.
JP 7059597A Japanese patent application (Mar. 5, 1995)—Paterra® InstantMT® Machine Translation—13 pages.
JP 2004018501A Japanese patent application (Jan. 22, 2004)—abstract (Derwent Information Ltd)—1 page.
JP 2004018501A Japanese patent application (Jan. 22, 2004)—Paterra® InstantMT® Machine Translation—38 pages.
WO00/32808A1—abstracts (Derwent Information Ltd; HCAPLUS/ACS on STN)—2 pages, Jun. 8, 2000.
WO00/32808 A1 (Jun. 8, 2000)—part, post-edited machine translation (Rising Sun Communications)—2 pages.
JP 2002223794A Japanese patent application (Aug. 13, 2002)—machine translation (from European Patent Office file EP1735457)—20 pages.
JP 4220603B2 Japanese patent (Feb. 4, 2009)—claims translation (Patent Agent)—4 pages.
JP 4220603B2 Japanese patent (Feb. 4, 2009)—translation (Multilingual Solutions)—30 pages.
JP 4220603B2 Japanese patent (Feb. 4, 2009)—Paterra® InstantMT® Machine Translation (55 pages); post-edited claims (Lionbridge; 6 pages).
Abstract—Science Links Japan (1 page): Ito T, et al., "Serum PAF-Acetylhydrolase (PAF-AH) in Hepatobiliary Disease," Japanese Pharmacology and Therapeutics (2002) 30/Suppl. 2.
Abstract—HCAPLUS (1 Page): Kawamura Y, "A Simple Measurement of Plasma Platelet-Activating Factor (PAF) Acetylhydrolase, Normal Level Activity, and Distribution Among Lipoprotein Fractions," Japanese Journal of Clinical Pathology (Oct. 1987)35(10):1149-1153.
Abstract—HCAPLUS (1 Page): Masao Miwa, et al., "Serum platelet-activating factor (PAF) acetylhydrolase of children with bronchial asthma," Japanese Journal of Inflammation (1988)8(4):327-333.
EP1735457 (application No. EP 05779946) Supplemental European Search Report, EPO, Jul. 17, 2007, 2 pages.
Fujimura K. et al., "Serum Platelet-Activating Factor Acetylhydrolase Activity in Rats with Gastric Ulcers Induced by Water-Immersion Stress," *Scandinavian Jnl of Gastroenterology*, Suppl, (1989) 24/162 (59-62).
Hiramoto M et al., "A Mutation in Plasma Platelet-Activating Factor Acetylhydrolase (Val$^{279}$→Phe) is a Genetic Risk Factor for Stroke," *Stroke* (Dec. 1997) 28 (12) 2417-20.

Izaki S et al., "Platelet-activating factor and arachidonic acid metabolites in psoriatic inflammation," *British Jnl of Dermatology* (Jun. 1996) 134 (6) 1060-4.
Bell, et al.; Systematic Screening of the LDL-PLA2Gene for Polymorphic Variants and Case-Control Analysis in Schizophrenia; Biochem and Biophys Res. Commun.; 241(3); pp. 630-635; Dec. 29, 1997.
BISC 429 ("BISC 429: Experimental Techniques II Separation Methods, Acid Phosphatase-Enzyme Assay", Simon Fraser University available at www.sfu.ca/bisc/bisc-429/enzymeassay.html#intro, including image of Google search showing that the document has been available since Jan. 31, 2002.
Blankenberg, et al.; Plasma PAF-acetylhydrolase in patients with coronary artery disease: results of a cross-sectional analysis; J. Lipid Res; 44(7); pp. 1381-1386 May 1, 2003.
Furukawa, et al.; Platelet-Activating Factor Induced Ischemic Bowel Necrosis: The Effect of Platelet-Activating Factor Acetylhydrolase; Pediatr. Res; 34(2):237-41; Aug. 1993 Pediatr. Res; 34(2); 237-41; Aug. 1993.
Grissom, et al.; Platelet-activating factor acetylhydrolase is increased in lung lavage fluid from patients with acute respiratory distress syndrome; Critical Care Medicine; 31(3); 770-775; Mar. 2003.
Henderson, et al.; Recombinant Human Platelet-Activating Factor-Acetylhydrolase Inhibits Airway Inflammation and Hyperreactivity in Mouse Asthma Model; J. Immunol; 164(6): 3360-3367; Mar. 15, 2000.
Janeway, et al.: Immunobiology: The Immune System in Health and Disease; Garland Publishing; New York, NY; 3d Ed; pp. 3.1-3.11; 1997.
Khovidhunkit, et al.; Plasma platelet-activating factor acetylhydrolase activity in human immunodeficiency virus infection and the acquired immunodeficiency syndrome; Metabolism; 48(12); 1524-31; Dec. 1999.
McManus, et al.; PAF, a putative mediator of oral inflammation; Crit Rev Oral Bio Med; 11(2): 240-258; 2000.
Miller, et al.; U.S. Appl. No. 13/839,041 entitled: "Lipoprotein-associated phospholipase A2 antibody composition and methods of use." Filed Mar. 15, 2013.
Muguruma, et al.: The central role of PAF in necrotizing enterocolitis development: Adv. Exp Med. Biol. 407:379-82; 1997.
Montaner, et al.; U.S. Appl. No. 13/695,027 entitled: "Methods Using Lipoprotein-Associated Phospholipase A2 in an Acute Care Setting." Filed May 23, 2013.
Paul, W.E., ed.; Fundamental Immunology; Raven Press, 3d Ed.; p. 242; Nov. 1993.
Portolano, et al.; Lack of Promiscuity in Autoantigen-Specific H and L chain combinations as Revealed by Human H and L Chain "Roulette;" J. Immunolo; 159(3): 880-887; Feb. 1993.
Rattan, et al.: Protein synthesis, posttranslational modifications and aging; Ann N Y Acad Sci., 663:48-62; Nov. 21, 1992.
Rudikoff, et al.; single Amino Acid Substitution Altering antigen-binding Specificity; Proc Natl Acad Sci; 79: 1979-1983; Mar. 1982.
Satoh, et al.; Platelet-activating factor acetylhydrolase in plasma lipoproteins from patients with ischemic stroke; Stroke; 23(8); pp. 1090-1092; Aug. 1992.
Satoh et al.; Plasma platelet-activating factor acetylhydrolase deficiency in Japanese patients with asthma; Am. J. Respir Crit Care Med; 159(3); 974-9; Mar. 1999.
Seifter, et al.; Analysis for protein modifications and nonprotein cofactors; Methods Enzymol; 182:626-46; 1990.
Serebruany, et al., Depressed Plasma Platelet-Activating Factor Acetylhydrolase in Patients Presenting with Acute Myocardial Infarction; Cardiology; 90(2):127-130; Oct. 1998.
Shou et al.; U.S. Appl. No. 13/540,571, entitled "Methods for Detecting LP-PLA2 Activity and Inhibition of LP-PLA2 Activity ", filed Jul. 2, 2012.
Stafforini et al.; Human macrophages secrete platelet-activating factor acetylhydrolase; Journal of Biological Chemistry; 265(17); pp. 9682-9687; Jun. 1990.
Stremler, et al.; An oxidized derivative of phosphatidylcholine is a substrate for the platelet-activating factor acetylhydrolase from human plasma; J. Biological Chem; 264(10); pp. 5331-5334; Apr. 1989.

(56) References Cited

OTHER PUBLICATIONS

TJoelker, et al.; Anti-inflammatory properties of a platelet-activating factor acetylhydrolase; Nature 374, 549-553; Apr. 6, 1995.

Tselepis, et al.; Association of the inflammatory state in active juvenile rheumatoid arthritis with hypoRhigh-density lipoproteinemia and reduced lipoprotein-associated platelet-activating factor acetylhydrolase activity; Arthritis Rheum.; 42(2); 373-383; Feb. 1999.

Tselepis, et al.; Inflammation, bioactive lipids and atherosclerosis: potential roles of a lipoprotein-associated phospholipase A2, platelet activating factor-acetylhydrolase; Atheroscler Suppl; 3(4):57-68; Dec. 2002.

Tsuji, et al.; The presence of platelet-activating factor-acetylhydrolase in human middle ear effusions; ORL J. Otorhinolaryngol Relat Spec.; 60(1); 25-9; Jan.-Feb. 1998.

Washburn, et al., Novel general approach for the assay and inhibition of hydrolytic enzymes utilizing suicide-inhibitory bifunctionally linked substrates (SIBLINKS); Exemplified by a phospholipase A2 assay; J. Am. chem.. Soc; 112 pp. 2040-2041; Feb. 1990.

Washburn, et al.; Suicide-inhibitory bifunctionally linked substrates (SIBLINKS) as phospholipase A2 inhibitors; J. Biological Chem; 266(8); pp. 5042-5048; Mar. 1991.

Yoon, et al.; Interdependent effect of angiotensin-converting enzyme and platelet-activating factor acetylhydrolase gene polymorphisms on the progression of immunoglobulin A nephropathy; Clinical Genetics; 62(2): 128-134; Aug. 2002.

Yoshida, et al.; Platelet-activating factor acetylhydrolase in red cell membranes. Does decreased activity impair erythrocyte deformability in ischemic stroke patients? Stroke; 24(1); pp. 14-18; Jan. 1993.

MacPhee, et al.; U.S. Appl. No. 13/208,015 entitled "Lipoprotein Associated Phospholipase A2, Inhibitors Thereof and Use of the Same in Diagnosis and Therapy." filed Aug. 11, 2011.

METHODS FOR DETECTING LP-PLA2 ACTIVITY AND INHIBITION OF LP-PLA2 ACTIVITY

CROSS-REFERENCE TO PREVIOUS APPLICATION

This application is a continuation of U.S. Ser. No. 11/106,239, filed on Apr. 14, 2005, now U.S. Pat. No. 7,741,020, which claims benefit of U.S. Provisional Application No. 60/563,078, filed Apr. 16, 2004, the entirety of which is incorporated by reference.

FIELD OF THE INVENTION

This invention relates generally to methods and materials for determining lipoprotein-associated phospholipase A2 (herein "Lp-PLA2") enzyme activity and inhibition of activity in tissue samples from animals.

BACKGROUND OF THE INVENTION

Coronary heart disease (herein "CHD") is the leading cause of death in many industrial countries. Atherosclerosis is a form of arteriosclerosis or hardening of the arteries in which there is the progressive build-up of plaque containing cholesterol and lipids in blood arteries. This build-up is associated with an increased risk of heart disease and morbid coronary events. The build-up of plaque in the arteries is associated with an immune response that is triggered by damage to the endothelium. Initially, monocyte-derived macrophages accumulate at the damaged site, due to the immune response causing a migration and accumulation of smooth muscle cells which form fibrous plaque in combination with the macrophages, lipids, cholesterol, calcium salts and collagen. The growth of such lesions can eventually block the artery and restrict blood flow.

Lp-PLA2, also known as PAF acetylhydrolase, is a secreted, calcium-independent member of the growing phospholipase A2 superfamily (Tew, et al. (1996) *Arterioscler Thromb Vasc Biol.* 16(4):591-9; Tjoelker, et al. (1995) *Nature* 374(6522):549-53). It is produced by monocytes, macrophages, and lymphocytes and is found associated predominantly with LDL (~80%) in human plasma. The enzyme cleaves polar phospholipids, including sn-2 ester of 1-O-alkyl-2-scetyl-sn-glycero-3-phosphocholine, otherwise known as platelet-activating factor (herein "PAF") (Tjoelker, et al. (1995) *Nature* 374(6522):549-53).

Many observations have demonstrated a pro-inflammatory activity of oxidized LDL when compared with native unmodified lipoproteins. One of the earliest events in LDL oxidation is the hydrolysis of oxidatively modified phosphatidylcholine, generating substantial quantities of lysophosphatidylcholine (herein "lyso-PC") and oxidized fatty acids. This hydrolysis is mediated solely by Lp-PLA2 (i.e., Lp-PLA2 hydrolyzes PAF to give lyso-phosphatidylcholine [herein "lyso-PC"] and acetate). (Stafforini, et al. (1997) *J. Biol. Chem.* 272, 17895)

Lyso-PC is suspected to be a pro-inflammatory and pro-atherogenic mediator. In addition to being cytotoxic at higher concentrations, it is able to stimulate monocyte and T-lymphocyte chemotaxis, as well as induce adhesion molecule and inflammatory cytokine expression at more modest concentrations. Lyso-PC has also been identified as the component of oxidized LDL that is involved in the antigenicity of LDL, a feature that may also contribute to the inflammatory nature of atherosclerosis. Moreover, lyso-PC promotes macrophage proliferation and induces endothelial dysfunction in various arterial beds. The oxidized fatty acids that are liberated together with lyso-PC are also monocyte chemoattractants and may also be involved in other biological activities such as cell signaling). Because both of these products of Lp-PLA2 hydrolysis are potent chemoattractants for circulating monocytes, Lp-PLA2 is thought to be responsible for the accumulation of cells loaded with cholesterol ester in the arteries, causing the characteristic "fatty streak" associated with the early stages of atherosclerosis.

Lp-PLA2 has also been found to be enriched in the highly atherogenic lipoprotein subfraction of small dense LDL, which is susceptible to oxidative modification. Moreover, enzyme levels are increased in patients with hyperlipidaemia, stroke, Type 1 and Type 2 diabetes mellitus, as well as in post-menopausal women. As such, plasma Lp-PLA2 levels tend to be elevated in those individuals who are considered to be at risk of developing accelerated atherosclerosis and clinical cardiovascular events. Thus, inhibition of the Lp-PLA2 enzyme would be expected to stop the build up of this fatty streak (by inhibition of the formation of lysophosphatidylcholine), and so be useful in the treatment of atherosclerosis.

Lp-PLA2 inhibitors inhibit LDL oxidation. Lp-PLA2 inhibitors may therefore have a general application in any disorder that involves lipid peroxidation in conjunction with the enzyme activity, for example in addition to conditions such as atherosclerosis and diabetes other conditions such as rheumatoid arthritis, stroke, myocardial infarction (Serebruany, et al. *Cardiology.* 90(2):127-30 (1998)); reperfusion injury and acute and chronic inflammation. In addition, Lp-PLA2 is currently being explored as a biomarker of coronary heart disease (Blankenberg, et al. *J Lipid Res.* 2003 May 1) and arteriosclerosis (Tselepis and Chapman. *Atheroscler Suppl.* 3(4):57-68 (2002)). Furthermore, Lp-PLA2 has been shown to play a role in the following disease: respiratory distress syndrome (Grissom, et al. *Crit. Care Med.* 31(3): 770-5 (2003); immunoglobulin A nephropathy (Yoon, et al. *Clin Genet.* 62(2):128-34 (2002); graft patency of femoropopliteal bypass (Unno, et al. *Surgery* 132(1):66-71 (2002); oral inflammation (McManus and Pinckard. *Crit. Rev Oral Biol Med.* 11(2):240-58 (2000)); airway inflammation and hyperreactivity (Henderson, et al. *J Immunol.* 15; 164(6): 3360-7 (2000)); *HIV and AIDS* (Khovidhunkit, et al. *Metabolism.* 48(12):1524-31 (1999)); asthma (Satoh, et al. *Am J Respir Crit. Care Med.* 159(3):974-9 (1999)); juvenile rheumatoid arthritis (Tselepis, et al. *Arthritis Rheum.* 42(2):373-83 (1999)); human middle ear effusions (Tsuji, et al. *ORL J Otorhinolaryngol Relat Spec.* 60(1):25-9 (1998)); schizophrenia (Bell, et al. *Biochem Biophys Res Commun.* 29; 241 (3):630-5 9 (1997)); necrotizing enterocolitis development (Muguruma, et al. *Adv Exp Med. Biol.* 407:379-82 (1997)); and ischemic bowel necrosis (*Pediatr Res.* 34(2):237-41 (1993)).

Lp-PLA2 activity from human tissue samples has been measured using spectrophotometric activity and fluorogenic activity assays (Cayman Chemical Company, and Karlan Research Products). See also Kosaka, et al. *Clin Chem Acta* 296(1-2):151-61 (2000) and Kosaka, et al. *Clin Chem Acta* 312(1-2):179-83 (2001). For instance, Azwell, Inc. (Osaka, Japan) reported in 2000 the synthesis and use of 1-myristoyl-2-(p-nitrophenylsuccinyl) phosphatidylcholine as a colorimetric substrate for measurement of human PAF AH (Lp-PLA2) activity in plasma and serum. In 2002, Azwell launched its research-use-only Auto PAF AH assay kit that utilizes this substrate and is formatted for use in a clinical chemistry analyzer. These methods may be capable of detecting inhibition of Lp-PLA2 activity when an inhibitor of Lp- PLA2 is added to a tissue sample in vitro. However, the methods provided with the Auto PAF AH assay are insensitive to measuring inhibition of Lp-PLA2 activity when an inhibitor of Lp-PLA2 has been administered to an animal prior to tissue sample collection.

In order to measure Lp-PLA2 activity in the presence of inhibitor in a tissue sample obtained from an animal administered inhibitor, an activity protocol is required. Accordingly, methods for determining LP-PLA2 activity and inhibition from a tissue sample obtained from an animal that has been administered an Lp-PLA2 inhibitor are greatly needed.

SUMMARY OF THE INVENTION

In one aspect of the present invention, a method is provided for determining inhibition of Lp-PLA2 enzyme activity in at least one tissue sample comprising the steps of preparing a solution comprising a substrate for Lp-PLA2 comprising a colorimetric or fluorometric detectable moiety; contacting at least one said tissue sample with the solution of the preparing step; and detecting Lp-PLA2 activity, wherein the tissue sample is from an animal that has been administered with Lp-PLA2 inhibitor.

In another aspect of the current invention, a method is provided for determining Lp-PLA2 enzyme activity in a tissue sample obtained from an animal comprising the steps of:
a) contacting 110 μL of a solution comprising:
   a solution comprising 90 mM 1-myristoyl-2-(4-nitrophenylsuccinyl) phosphatidylcholine contacted with a solution comprising 200 mM HEPES, 200 mM NaCl, 5 mM EDTA, 10 mM CHAPS, 10 mM sodium 1-nonanesulfonate at a pH 7.6 in a ratio of 0.66 μL to 110 μL;
with at least one 25 μL tissue sample from an animal;
with 25 μL each of a p-nitrophenol standard solution comprising; 4, 3, 2, 1, 0.4 or 0.2 nmol/μL p-nitrophenol in methanol; and
25 μL of phosphate buffered saline (PBS) or ddH$_2$O to make a blank; and
b) determining Lp-PLA2 activity.

DETAILED DESCRIPTION OF THE INVENTION

Glossary

"Animal" as used herein includes any human or non-human mammal, or any other vertebrate capable of naturally producing an enzyme having Lp-PLA2 activity, including Lp-PLA2, Lp-PLA2—homologs or orthologs thereof.

"Clinical trial" means human clinical trial.

"Lp-PLA2 enzyme activity" as used herein includes, but is not limited to, any enzyme activity of Lp-PLA2. This activity may include but is not limited to an Lp-PLA2 enzyme binding substrate, releasing product, and/or hydrolyzing phospholipids or other molecules.

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may comprise amino acids other than the 20 gene encoded amino acids. "Polypeptide(s)" comprise those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may comprise many types of modifications. Modifications can occur anywhere in a polypeptide, including the peptide backbone, the amino acid side-chains, and the amino or carboxyl termini. Modifications comprise, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, PROTEINS—STRUCTURE AND MOLECULAR PROPERTIES, 2nd Ed., T. E. Creighton, W.H. Freeman and Company, New York (1993) and Wold, F., Posttranslational Protein Modifications: Perspectives and Prospects, pgs. 1-12 in POSTTRANSLATIONAL COVALENT MODIFICATION OF PROTEINS, B. C. Johnson, Ed., Academic Press, New York (1983); Seifter et al., Meth. Enzymol. 182:626-646 (1990) and Rattan et al., Protein Synthesis: Posttranslational Modifications and Aging, Ann. N.Y. Acad. Sci. 663: 48-62 (1992). Polypeptides may be branched or cyclic, with or without branching. Cyclic, branched and branched circular polypeptides may result from post-translational natural processes and may be made by entirely synthetic methods, as well.

"Filtration" or "filtering" as used herein includes, but is not limited to, the removal of any substance from a solution and may comprise passing a solution containing the substance to be removed through filter paper, Whatman paper, cheese cloth, or a column that selectively removes said substance from solution based on its physical and/or chemical characteristics. Physical and chemical characteristics that may be used to remove a substance through filtration may include, but are not limited to, ionic charge, size, weight, polarity, and/or chemical moieties associated with the substance that make it likely to bind to the material filling the column. Filtration may comprise using gravity, vacuum, and/or centrifugation to facilitate the removal of said substance from solution.

"Scintillation cocktail" as used herein is a mixture of solutes and solvents, typically containing an organic solvent capable of solubilizing and maintaining a uniform suspension of a tissue sample for liquid scintillation. The process of liquid scintillation involves the detection of beta decay within a sample via capture of beta emissions. A scintillation cocktail mixture is designed to capture the beta emission and transform it into a photon emission which can be detected via a photomultiplier tube within a scintillation counter. Several scintillation cocktails are commercially available. It is understood that a modification of the composition of the scintillation cocktail can effect and/or optimize the detectable reading from liquid scintillation depending on the sample.

"Tissue(s)" as used herein comprises serum, cell lysate, tissue lysate, urine, blood plasma, plaque, monocytes, or macrophage cells. These tissues can be from humans, non-human mammals or other animals that naturally produces and enzyme having Lp-PLA2 activity, including Lp-PLA2, Lp-PLA2—homologs or orthologs thereof.

"Colorimetric or fluorimetrc detectable moiety" as used herein is a portion of a compound capable of producing a detectable or measurable signal. Such a signal may be measurable by, but not limited to, visible light emission or absorption, fluorescence, phosphorescence or other detectable quanta. For instance, a substrate for Lp-PLA2 may comprise a colorimetric c moiety bonded to phosphatidylcholine at the Lp-PLA2 cleavage site. When Lp-PLA2 cleaves the colorimetric moiety from phosphatidylcholine the colorimetric moiety emits a detectable signal as visible light. One non-limiting example of phosphatidylcholine bonded to a colorimetric moiety is 1-myristoyl-2-(4-nitrophenylsuccinyl) phosphatidylcholine.

Lp-PLA2 "inhibitor" or "inhibition" as used herein refers to any method, technique, condition, or compound capable of reducing or eliminating Lp-PLA2 activity, including but not limited to reducing or eliminating any of the activities of Lp-PLA2 including, but not limited to, enzyme binding substrate, releasing product, and/or hydrolyzing phospholipids or other molecules. Inhibition of Lp-PLA2 activity may be measured in a sample obtained from an animal administered an inhibitor, which is considered in vivo administration. Alternatively, an inhibitor may be added to a sample after it is obtained from an animal, which would be considered in vitro administration.

considered essentially free of inhibitor. A tissue sample may be considered free of Lp-PLA2 inhibitor if it is obtained from an animal prior to administration of an Lp-PLA2 inhibitor that is not produced naturally by the animal. A tissue sample may also be considered free or essentially free of an Lp-PLA2 inhibitor if it is obtained from an animal at a time after the last dose of inhibitor sufficient to ensure clearance based on pharmacokinetic profile of that inhibitor in the species of animal.

Lp-PLA2 is a known hydrolyzer of phospholipids. Lp-PLA2 can cleave phospholipids at the sn-2 position to create lyso-PC and oxidized fatty acids. PAF has a two-carbon acyl group at the sn-2 position; therefore, when PAF is hydrolyzed by Lp-PLA$_2$, the short acyl group is cleaved as water soluble acetate from the remainder of the molecule, which is lyso-PC. A substrate possessing a colorimetric or fluorimetrc moiety can be used to measure Lp-PLA2 activity. For instance, the substrate, 1-myristoyle-2-(p-nitrophenylsuccinyl)-phosphatidylcholine, is a PAF analogue with a 4-nitrophenyl group conjugated onto a succinyl chain at sn-2 position. Lp-PLA2 (PAF-AH) hydrolyzes the sn-2 position of the substrate, producing 4-nitrophenyl succinate. This liberation can be spectrophotometrically monitored at 405 nm and Lp-PLA2 activity determined from the change in absorption.

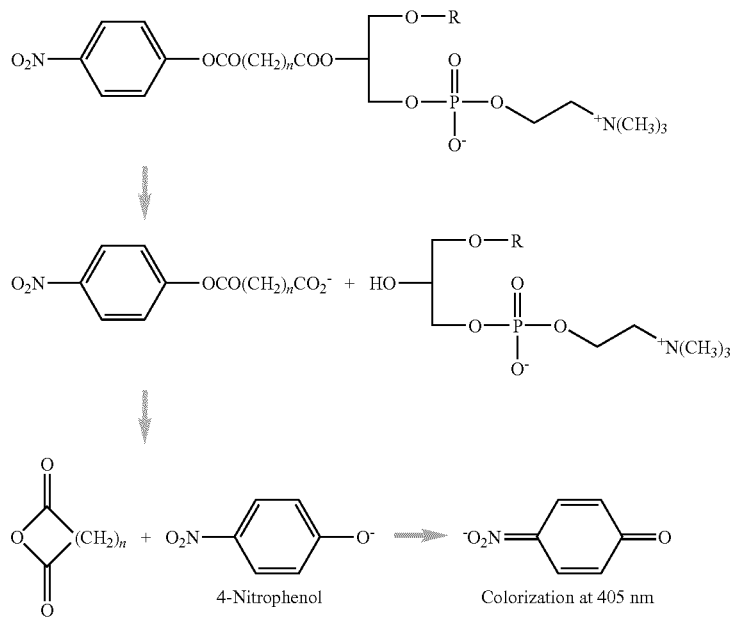

As used herein, "reduce" or "reducing" refers to a decrease or elimination in Lp-PLA2 enzyme activity. Some non-limiting examples for the purposes of measuring reduced Lp-PLA2 activity include measuring Lp-PLA2 activity from the same animal in the presence and absence of an inhibitor of Lp-PLA2 activity. Alternatively, Lp-PLA2 activity can be measured against a standard recombinantly expressed, semi-purified or purified enzyme.

As used herein "free" or "essentially free" of Lp-PLA2 inhibitor refers to a tissue sample that contains either no Lp-PLA2 inhibitor or Lp-PLA2 inhibitor at a low enough concentration such that Lp-PLA2 activity is not inhibited by the inhibitor. For instance, if the inhibitor is present at a concentration lower than the determined dissociation constant of that inhibitor for Lp-PLA2, a tissue sample may be The methods of the present invention have been shown to demonstrate a correlation between Lp-PLA2 inhibitor concentration in a tissue sample and Lp-PLA2 activity in vitro. Furthermore, the present invention provides methods for measuring Lp-PLA2 activity over time in tissue samples from animals treated with Lp-PLA2 inhibitor. These data may be correlated with the pharmacokinetic profile of inhibitor from an animal, such as a human.

A colorimetric Lp-PLA2 activity monitoring assay has been developed using 1-myristoyl-2-(p-nitrophenylsuccinyl) phosphatidylcholine as the substrate. In vitro drug inhibition study using Lp-PLA2-specific inhibitors showed specificity of this substrate against Lp-PLA2. However, the Auto PAF AH assay provided by Azwell failed to detect drug inhibition in human subjects who received Lp-PLA2 inhibitor drugs in vivo, although the same substrate and the same buffer condition are used in the assays developed herein. Factors such as pre-incubation of plasma with assay buffer, plasma sample volume, substrate concentration, and use of buffer R2A, have been identified to contribute to in vitro drug dissociation in the assay and in turn cause the inability of the assay to detect drug inhibition in in vivo drug-bound tissue samples. These factors therefore were modified in development of new, drug-sensitive colorimetric Lp-PLA2 activity assays. Interactions between these factors have also been studied so that assay conditions could be chosen that would generate detectable in vivo drug inhibition and also offer an adequate assay dynamic range. This modified drug-sensitive assay is able to detect 85-95% drug inhibition in human subjects with in vivo administration of Lp-PLA2 inhibitors and therefore could be used as a monitoring assay to assess drug efficacy in the clinic. This assay also offers a dynamic range of close to 100-fold and potentially is also useful as a screening assay that is capable of measurement of a broader range of Lp-PLA2 activity.

In one aspect of the present invention, a method is provided for determining inhibition of Lp-PLA2 enzyme activity in at least one tissue sample comprising the steps of preparing a solution comprising a substrate for Lp-PLA2 comprising a colorimetric or fluorometric detectable moiety; contacting at least one said tissue sample with the solution of the preparing step; and detecting Lp-PLA2 activity, wherein the tissue sample is from an animal that has been administered with Lp-PLA2 inhibitor. These methods may further comprise comparing Lp-PLA2 activity from a tissue sample obtained from an animal prior to Lp-PLA2 inhibitor administration or that is free of Lp-PLA2 inhibitor. Inhibition of Lp-PLA2 activity may be measured in a plurality of tissue samples obtained from an animal at more than one time point after administration of said Lp-PLA2 inhibitor. The substrate may be 1-myristoyl-2-(4-nitrophenylsuccinyl) phosphatidylcholine and may be used at a concentration of about 53 µM to about 1125 µM. The concentration of -myristoyl-2-(4-nitrophenylsuccinyl) phosphatidylcholine may be 440 µM or it may be 112 µM.

In one aspect of the invention, the tissue sample may be blood plasma, or it may be serum. In another aspect, the blood plasma is diluted about 3 to 9 fold with the solution of the preparing. Lp-PLA2 activity may be measured by measuring optical density of the tissue sample.

In another aspect of the present invention, the solution comprising a substrate for Lp-PLA2 further comprises a buffer and wherein the buffer is incubated with the substrate prior to contacting the substrate with said tissue sample. In another aspect, the buffer does not comprise citric acid monohydrate. In another aspect, the substrate concentration is maintained at approximately the Km of said substrate. Km of said substrate may be decreased by removing citric acid monohydrate from the buffer. When the substrate is 1-myristoyl-2-(4-nitrophenylsuccinyl) phosphatidylcholine, the substrate concentration may be about 440 µM or may be about 112 µM.

In another aspect of the present invention, the volume of plasma sample is about 15 µL to about 50 µL in a volume of about 125 µL to about 170 µL of the solution of the preparing step. In another aspect, the pH of the reaction is maintained at least about 7.5 prior to contacting the plasma sample with the solution of the preparing step.

In another embodiment of the present invention, a method is provided for determining Lp-PLA2 enzyme activity in a tissue sample obtained from an animal comprising the steps of:

a) contacting 110 µL of a solution comprising:
a solution comprising 90 mM 1-myristoyl-2-(4-nitrophenylsuccinyl) phosphatidylcholine contacted with a solution comprising 200 mM HEPES, 200 mM NaCl, 5 mM EDTA, 10 mM CHAPS, 10 mM sodium 1-nonanesulfonate at a pH 7.6 in a ratio of 0.66 µL to 110 µL; with at least one 25 µL tissue sample from an animal;
with 25 µL each of a p-nitrophenol standard solution comprising; 4, 3, 2, 1, 0.4 or 0.2 nmol/µL p-nitrophenol in methanol; and
25 µL of phosphate buffered saline (PBS) or ddH$_2$O to make a blank; and
b) determining Lp-PLA2 activity.

In one aspect, the tissue sample from animal is blood plasma. In another aspect, the animal is human. In yet another aspect, the animal has been administered an inhibitor of Lp-PLA2 prior to obtaining the tissue sample. Inhibition of Lp-PLA2 enzyme activity by said Lp-PLA2 inhibitor administered prior to obtaining said tissue sample is measured by comparing Lp-PLA2 activity of a tissue sample free of said Lp-PLA2 inhibitor.

In another embodiment of the present invention, a method is provided for determining Lp-PLA2 enzyme activity in a tissue sample obtained from an animal wherein enzyme activity is determined by:

a) generating a standard curve by plotting optical density (OD) values at 405 nm for the p-nitrophenol standard solutions vs. p-nitrophenol (nmol/well);
b) calculating the slope (OD/nmol) of the standard curve;
c) calculating aborbance change between 3 and 1 minute ($\Delta OD_{3min-1min}$) for both solutions comprising tissue samples and blank; and
d) calculating Lp-PLA2 activity using the following formula:

$$Lp\text{-}PLA2 \text{ activity(nmol/min/ml)} = (\Delta OD_{sample} - \Delta OD_{blank}) \div \text{slope (OD/nmol)} \div 0.025 \text{ ml} = 2 \text{ minutes}.$$

In another embodiment of the present invention, a method is provided for determining Lp-PLA2 enzyme activity in a tissue sample obtained from an animal comprising the steps of:

a) preparing a solution comprising 200 mM HEPES, 200 mM NaCl, 5 mM EDTA, 10 mM CHAPS, 10 mM sodium 1-nonanesulfonate at a pH 7.6;
b) preparing a solution comprising 90 mM 1-myristoyl-2-(4-nitrophenylsuccinyl) phosphatidylcholine;
c) preparing 100, 75, 50, 25, 10 and 5 nmol/µL stock solutions of p-nitrophenol in methanol;
d) preparing working solutions for p-nitrophenol standards by diluting 40 µL of stock solutions of step c into 960 µL of methanol;
e) contacting the solution of step b and the solution of step a in a ratio of 0.66 µL to 110 µL to make an assay buffer;
f) adding 120 µL of assay buffer to each well in a 96-well V-bottom plate;
g) adding 25 µL of each p-nitrophenol standard working solution of step d into a separate well of two columns of a 96-well flat-bottom plate;
h) adding 25 µL of tissue sample from an animal per well that do not contain p-nitrophenol standards of the flat-bottom plate of step g;
i) adding 25 µL of PBS or dd H$_2$O into an empty well in the flat-bottom plate for use as a blank;
j) contacting 110 µL of assay buffer from the V-bottom plate to each well of the flat-bottom assay plate;
k) placing the flat bottom assay plate onto a plate reader and reading at 405 nm;

l) generating a standard curve by plotting optical density (OD) values for the standard solutions vs. p-nitrophenol (nmol/well);
m) calculating the slope (OD/nmol) of the standard curve;
n) calculating absorbance change between 3 and 1 minutes ($\Delta OD_{3min-1min}$) for both test samples and the blank; and
o) calculating Lp-PLA2 activity using the following formula:

$Lp\text{-}PLA2$ activity(nmol/min/ml)=($\Delta OD_{sample}$ − $\Delta OD_{blank}$)÷slope (OD/nmol)÷0.025 ml÷2 minutes.

Calculating the absorbance change can be performed at various intervals including, but not limited to, 2 and 0 minutes, 1 and 0 minutes and about 15-second intervals measured over about a 10 minute reaction time.

The following examples illustrate various aspects of this invention. These examples do not limit the scope of this invention which is defined by the appended claims.

EXAMPLES

Unless otherwise indicated all plasma samples were collected from human and are human plasma. Unless otherwise indicated, plasma samples for the following examples were collected as follows. Blood was collected into EDTA-containing tubes. The tubes were centrifuged at 1730×g for 10 minutes. Plasma was drawn off with transfer pipettes into tubes and stored at −80° C.

In experiments in which Lp-PLA2 inhibitor was added to tissue samples in vitro the following procedure was used, unless otherwise indicated. A 9 mg/mL stock solution was prepared in PBS. A series of working dilutions were prepared in PBS to give concentrations of 90000, 9000, 6000, 3000, 1000, 500, 200, 100, and 0 ng/mL. One microliter of each working dilution was added to every 100 ul of plasma or serum followed by incubation at 37° C. for 1 hour. The final concentrations of Lp-PLA2 inhibitor in plasma or serum were: 900, 90, 60, 30, 10, 5, 2, 1, and 0 ng/mL.

Example 1

The Auto PAF AH Assay Kit

The Auto PAF AH assay kit, manufactured by Azwell (Osaka, Japan), is commercially available in the United States through Karlan Research Products Corporation (Santa Rosa, Calif.). This assay was evaluated on an Olympus Au640 clinical chemistry analyzer and is described in this Example 1.
Materials
Azwell Auto PAF-AH Assay Kit:
R1: 200 mM HEPES, 200 mM NaCl, 5 mM EDTA, 10 mM CHAPS, 10 mM sodium 1-nonanesulfonate, pH 7.6
R2A: 20 mM citric acid monohydrate, 10 mM sodium 1-nonanesulfonate, pH 4.5
R2B: 90 mM 1-myristoyl-2-(4-nitrophenylsuccinyl) phosphatidylcholine
Assay Procedure
1. Enter assay parameters from the following table into the Olympus Au640 analyzer, and create a PAF AH assay program:
Sample volume: 2 μL
Reagent 1: 240 μL
Reagent 2: 80 μL
Wavelength (main): 410 nm
Wavelength (sub): 480 nm
Method: Rate
Point 1 (FST): 14
Point 1 (LST): 21
Calibration Type: MB
Formula: Y=AX+B
Counts: 2
MB Type Factor: 11595
2. Prepare the following reagents:
R1: Use this buffer solution as supplied in Azwell Auto PAF AH assay kit. Store at 4° C. Protect from light.
R2: Prepare the R2 working solution by mixing R2A and R2B (supplied in Azwell Auto PAF AH assay kit) in the proportion of 19:1. Store at 4° C. Protect from light.
3. Aliquot 30 μL or more of each plasma sample into a 2 mL Sarstedt micro-tubes (Sarstedt Incorporation, part No. 72.694.007). Briefly centrifuge to spin down fibrin clots/particles in the plasma.
4. Place Sarstedt tubes containing plasma samples onto sample tubes that fit the instrument. Run plasma samples through the Au640 analyzer. After choosing the PAF AH assay program, the analytical procedure described below is performed automatically:
Test sample (2 μL)+R1 (240 μL), 37° C., 5 minutes [0-5 minutes]
Add R2 (80 μL), 37° C., 5 minutes [5-10 minutes]
Measure the absorbance at 410 nm and 480 nm [6-8 minutes]
Calculate PAF AH activity (IU/L)
5. Include Bio-Rad Lyphochek Assayed Chemistry Control Level 1 and Level 2 (C-310-5 and C-315-5, Bio-Rad, Hercules, Calif.) as quality controls in each run. The Lp-PLA2 activity values for these two controls are within the range of normal human plasma Lp-PLA2.

Example 2

High Throughput Radiometric Assay for Measurement of Lp-PLA2 Activity

A high throughput radiometric assay was developed for measuring Lp-PLA2 activity in a sample. This assay is fully described in WO2005/001416. A summary of a high throughput radiometric activity assay is provided in this Example 2.

| Equipment | |
|---|---|
| Scintillation Counter | TopCount Microplate Scintillation and Luminescence Counter, Perkin-Elmer (formerly Packard), CA |
| Centrifuge | Allegra 25R benchtop centrifuge, Beckman Coulter, CA |
| Plate shaker | Lab-Line Titer Plate Shaker (VWR cat #57019-600) |
| Oven | Barnstead/Thermolyne, series 9000, temperature range 10-250° C. (VWR cat #52205-065) |
| 12-channel Pipettors | BRAND Transferpette ® -12, BrandTech Scientific, Inc., Essex, CT |
| Material | |
| Polypropylene Plates | Costar* Brand 96-Well Plates, Polypropylene, Nonsterile, Without Lids, Costar 3365, Corning, Inc., Corning, NY (VWR cat #29444-104) |
| PicoPlate Plates | 96-Well white solvent-resistant microplates, Perkin Elmer Life Sciences, Inc, Boston, MA (cat #6005162) |

Reagents
HEPES (4-(2-hydroxyethyl)-1-piperazineethane sulfonic acid) Sigma Chemical Co., St. Louis Mo. (Cat # H9897100)
Sodium Chloride, Sigma Chemical Co., St. Louis Mo. (Cat # S5150; 5.0 M)
EDTA, Sigma Chemical Co., St. Louis Mo. (Cat # E7889; 0.5 M)

³H-Platelet Activating Factor, 1-O-Hexadecyl-[acetyl-³H(N)], (³H-PAF)—NEN Life Science Products, Roxbury, Mass. (Cat # NET-910, supplied as an ethanol solution, typically 0.1 mCi/mL; 250 uCi)

C16-PAF, (1-hexadecyl-2-acetyl-sn-glycero-3-phosphocholine): Avanti Polar Lipids, Alabaster, Ala. (Cat #878110; 5.0 mg/ml)

MicroScint-20: Perkin Elmer Biosciences, Boston, Mass. (cat #6013621)

Fatty acid-free bovine serum albumin (BSA): Sigma Chemical Co., St. Louis Mo. (Cat # A0281; 1.0 gm)

Trichloroacetic acid (TCA): Sigma Chemical Co., St. Louis Mo. (Cat #T9159)

Assay Buffer
100 mM Hepes, pH 7.4
150 mM NaCl
5 mM EDTA
Store it at room temperature Procedures 1. Prepare a ³H-PAF working solution (for 100 reactions):
   a) Aliquot 480 μl ³H-PAF (10 μM=0.1 mCi/ml at 10.0 Ci/mmol) and 125.3 μl of [C16]PAF (5.0 mg/ml; MW: 524) to a tube;
   b) Mix and air dry in the hood;
   c) Resuspend the dried pellets in 12.0 ml of assay buffer giving working solutions of 100 μM PAF (i.e. ³H-PAF at 0.4 μM and cold [C16]PAF at 99.6 μM);
2. Aliquot 5 μL of assay buffer (for Total counts and Blanks; n=8) or plasma samples in duplicates into a 96-well plate;
3. Equilibrate the plate to 21° C.;
4. Add 100 μL of the ³H-PAF solution to each well, mix and incubate the plate at 21° C. for 5 minutes;
5. Add 50 μL of ice-cold BSA solution (50 mg/ml) to all wells, mix and incubate the plate in a refrigerator for 5 minutes;
6. Add 25 μL of ice-cold TCA solution (56%) to each well, mix and incubate the plate in a refrigerator for 15 minutes;
7. Centrifuge the plate at 6,000 g for 15 minutes at 4° C.;
8. Aliquot 45 μL of the supernatants to a 96-well polystyrene plate;
9. Add 10 μL of ³H-PAF working solution to 6 Total Counts wells;
10. Add 200 μL of MicroScint-20 scintillation cocktail to each well;
11. Cover the plate with a plate tape and vortex mix at max speed for 10 minutes;
12. Get static off the plate by wiping with a wet tissue and drying with another clean one;
13. Count with a TopCount scintillation counter for 2 minutes each; and
14. Calculate Lp-PLA2 activity:

$Lp\text{-}PLA2$ activity(nmoles/min/ml)=
$160*(CPM_{45\,\mu l\text{-}supe} - CPM_{Blanks})/(CPM_{10\,\mu l\text{-}spiking} - CPM_{Blanks})$ Where $CPM_{45\,\mu l\text{-}supe}$ is the average count from each sample
$CPM_{Blanks}$ is the average count of the Blanks
$CPM_{10\mu l\text{-}spiking}$ is the average count of the Total Counts Example 3

Correlation of Auto PAF AH Assay and High Throughput Radiometric Assay

A panel of 120 plasma samples from healthy human volunteers was assayed for Lp-PLA2 activity at three clinics using the high-throughput radiometric assay described in Example 2. The same sample panel was assayed using Azwell's Auto PAF AH assay described in Example 1 on the Olympus Au640 analyzer. Correlation was obtained against data generated on the same panel of samples by the high throughput radiometric assay. Correlation coefficients (r) were 0.96, 0.94, and 0.95 for Auto PAF AH vs. the radiometric activity assay at the three clinics, respectively. The average CV between duplicates was 2.14% for the Auto PAF AH assay.

Example 4

Low Throughput Radiometric Assay

A low throughput radiometric assay capable of measuring Lp-PLA2 activity is provided below.

| Materials | |
|---|---|
| Scintillation Vials | Wheaton Omni Vials, Millville, NJ (Cat # 225402) |
| Scintillation Fluid | EcoLite ™, ICN, Costa Mesa, CA (Cat # 882475) |
| Equipment | |
| Beta Counter | Beckman Liquid Scintillation Counter, LS 5000TA, Beckman Instruments, Fullerton, CA |
| Water Bath | Fisher Scientific, Edison, NJ |
| Microcentrifuge | Jouan Inc., Winchester, VA, Model No. A-14 |
| Reagents | |
| HEPES (4-(2-hydroxyethyl)-1-piperazineethane sulfonic acid) | Sigma Chemical Co., St. Louis MO (Cat # H 9136) |
| Sodium Chloride | Sigma Chemical Co., St. Louis MO (Cat # S 7653) |
| Chloroform | Aldrich Chemical Co., Milwaukee, WI (Cat # 36,692-7) |
| Methanol | Aldrich Chemical Co., Milwaukee, WI (Cat # 27,047-4) |
| ³H-Platelet Activating Factor, 1-O-Hexadecyl-[acetyl-³H(N)], (³H-PAF) | NEN Life Science Products, Roxbury, MA (Cat # NET-910, supplied as an ethanol solution, typically 0.1 mCi/mL) |
| C16-PAF, (1-hexadecyl-2-acetyl-sn-glycero-3-phosphocholine) | Avanti Polar Lipids, Alabaster, AL (Cat # 878110, supplied as 5 mg/mL CHCl₃ solution) |

Assay Buffer
HEPES/NaCl Buffer: 50 mM HEPES, 150 mM NaCl, pH 7.4 at 37° C.

Assay Solutions
³H-PAF working solution: Pipette 5 μCi (typically 50 μL of the solution supplied by the vendor) of H-PAF stock solution into a 1.4 mL glass vial. Add 340 ug (68 μL of a 5 mg/mL solution) of C16-PAF. Evaporate to dryness under a gentle stream of nitrogen gas in a fume hood. Reconstitute with 1.3 mL of HEPES/NaCl buffer. This will prepare sufficient working solution for approximately 62 assay tubes.

Assay Master Mix: In a 15 mL polypropylene tube, combine 7.3 mL of HEPES/NaCl buffer and 1.1 mL of ³H PAF working solution. In the final reaction mixture, after addition of the plasma sample, the final concentration of PAF (unlabelled C16-PAF+³H-PAF) is 50 uM (the 200 μL reaction volume contains 10 nmols PAF).

For testing the inhibition of LpPLA2 activity in plasma, the assay was performed as follows:

(1) 110 μL HEPES/NaCl buffer+20 μL of appropriate working dilution of Lp-PLA2 inhibitor+50 μL of plasma sample were added to a 1.5 mL microcentrifuge tube and incubated at 37° C. for 15 minutes.

(2) 20 μL of 3H-PAF working solution was added and the samples were incubated at 37° C. for 30 seconds.

(3) Reactions terminated by the addition of 600 μL of CHCl$_3$/CH$_3$OH and processed by the assay procedures described herein.

Assay Procedures

1. Thaw plasma samples and place in 37° C. water bath to temperature equilibrate.
2. Add 150 μL of assay master mix to 1.5 mL polypropylene tubes and place in 37° C. water bath. Allow 5 minutes for temperature equilibration.
3. Add 50 μL of plasma sample or 50 μL of HEPES/NaCl buffer for buffer blanks (all samples are assayed in duplicate) to appropriate tubes containing assay master mix, vortex briefly, and incubate for 30 seconds in the 37° C. water bath.
4. Stop reaction by addition of 600 μL of CHCl$_3$/CH$_3$OH solution and vortex well.
5. Just prior to centrifuging, briefly re-vortex the samples. Separate organic and aqueous phases by centrifugation in a microcentrifuge at maximum speed for 2 minutes.
6. Collect 250 μL of the upper, aqueous phase and transfer to a new 1.5 mL polypropylene tube.
7. Add 250 μL of CHCl$_3$ and vortex well.
8. Separate organic and aqueous phases by centrifugation in a microcentrifuge at maximum speed for 1 minute.
9. Collect 150 μL of the upper, aqueous phase and transfer to a 7 mL scintillation vial.
10. Add 2 mL of EcoLite™ or equivalent liquid scintillation fluid.
11. Count samples in liquid scintillation counter using a counting program that has been set up to determine cpm, counting efficiency, and dpm.
12. For determination of total radioactivity in the reaction, duplicate 150 μL aliquots of the assay master mix are counted.

Data Reduction and Analysis

Either cpm or dpm values may be used for calculation of Lp-PLA$_2$ activity. If the counting efficiency is the same for the samples, buffer blanks, and total radioactivity vials, cpm values may be used. If different counting efficiencies are observed, dpm values should be used. For all of the results in this report, dpm values were used for activity calculations.

The following equation is used to calculate LpPLA$_2$ activity (reported as nmols/min/mL) from the raw data:

$$((x-y)\div z)\times 40$$

where, x=cpm (or dpm) of plasma sample×1.65 (This corrects for the total volume of the aqueous phase in each extraction. This correction is necessary since only a portion of the aqueous phase is collected after each of the extractions.)

y=cpm (or dpm) of buffer blanks×1.65 (average of duplicate determinations)

z=cpm (or dpm) of total radioactivity samples divided by 10 (there are 10 nmols of PAF in each reaction tube (average of duplicate determinations)

40=factor to adjust results to nmol/min/mL (each reaction is for 30 seconds and the volume of plasma used in each reaction is 50 uL)

Example 5

Comparison of Inhibition of Lp-PLA2 Activity Measured by the Auto PAF AH Assay and Low Throughput Radiometric Assay Plasma was collected from six human subjects at different timepoints after in vivo drug administration of an Lp-PLA2 inhibitor during a clinical trial. Subjects #17 and #18 were dosed with 120 mg of Formula I, described below, subjects #24 and #25 with 180 mg, and subjects #21 and #22 with 240 mg. Subjects #21 and #25 also received placebo on a different day. Lp-PLA2 activity was measured by the low throughput radiometric assay, described in Example 4, and >90% inhibition was observed with all six drug-treated subjects. However, Lp-PLA2 inhibition was not apparent when measured by the Auto PAF AH assay, as described in Example 1. The Auto PAF AH assay is insensitive to in vivo drug inhibition of Lp-PLA2. See Table 1 below.

TABLE 1

Measurement of Lp-PLA2 Activity in Patients Who Received Inhibitor in vivo

Lp-PLA2 Activity (nmol/min/mL)

| | LTP Radiometric Assay | | | | | | Auto PAF AH Assay | | | | | |
| --- | --- | --- | --- | --- | --- | --- | --- | --- | --- | --- | --- | --- |
| Time (hr) | Drug #17 | Drug #18 | Drug #21 | Drug #22 | Drug #24 | Drug #25 | Drug #17 | Drug #18 | Drug #21 | Drug #22 | Drug #24 | Drug #25 |
| 0 | 36.19 | 29.82 | 16.03 | 32.14 | 39.13 | 19.08 | 402 | 349 | 197 | 345 | 459 | 205 |
| 0.5 | 34.25 | 3.70 | 8.19 | 30.25 | 35.38 | 18.86 | 346 | 303 | 192 | 353 | 398 | 177 |
| 1 | 17.33 | 2.10 | 1.39 | 27.43 | 3.53 | 2.52 | 410 | 260 | 239 | 345 | 426 | 178 |
| 2 | 3.82 | 1.30 | 0.62 | 8.76 | 1.48 | 0.71 | 338 | 296 | 214 | 332 | 336 | 178 |
| 3 | 2.04 | 1.77 | 0.79 | 4.61 | 1.11 | 0.51 | 333 | 299 | 217 | 357 | 482 | 196 |
| 4 | 1.83 | 1.82 | 0.88 | 1.58 | 1.02 | 0.45 | 333 | 297 | 206 | 350 | 502 | 194 |
| 6 | 1.22 | 2.33 | 1.06 | 1.18 | 1.49 | 0.53 | 297 | 295 | 184 | 350 | 402 | 186 |
| 12 | 3.38 | 4.72 | 2.19 | 2.91 | 3.26 | 1.56 | 321 | 295 | 197 | 353 | 538 | 157 |
| 24 | 6.05 | 7.05 | 3.87 | 5.06 | 6.65 | 3.46 | 413 | 323 | 235 | 362 | 547 | 229 |
| 32 | 7.31 | 6.55 | 3.17 | 3.59 | 7.85 | 4.15 | 346 | 296 | 242 | 350 | 530 | 213 |
| 48 | 10.62 | 9.64 | 5.34 | 5.82 | 10.29 | 5.42 | 475 | 287 | 211 | 321 | 537 | 221 |
| 96 | 18.31 | 14.65 | 10.22 | 12.38 | 16.88 | 11.05 | 463 | 322 | 227 | 341 | 569 | 245 |
| 144 | 29.31 | 18.51 | 14.26 | 17.72 | 25.14 | 17.14 | 452 | 324 | 224 | 369 | 502 | 313 |

Inter-run and within-run variability for the Auto PAF AH assay on the Olympus Au640 has been consistently low with CV less than 5% between replicates. In this experiment, the average CV between duplicates was 2% for placebo samples and 3% for all drug samples. However, Lp-PLA2 activity measured by the Auto PAF AH assay fluctuated over time for both drug and placebo subjects. Similarly, radiometric activity values for the placebo subjects fluctuated over time with a higher % CV compared with the Auto PAF AH assay. See Table 2 Observed variability in Lp-PLA2 activity for the placebo subjects appears to be biological variability.

TABLE 2

Lp-PLA2 Activity (nmol/min/mL) in Patients who Received Placebo and Inhibitor in vivo

| | Lp-PLA2 Activity (nmol/min/mL) | | | | | |
|---|---|---|---|---|---|---|
| | LTP Radiometric | | Auto PAF AH | | Auto PAF AH | |
| Time (hr) | Placebo #21 | Placebo #25 | Placebo #21 | Placebo #25 | Drug #21 | Drug #25 |
| 0 | 23.50 | 22.10 | 231 | 238 | 197 | 205 |
| 0.5 | 26.15 | 23.11 | 227 | 246 | 192 | 177 |
| 1 | 18.97 | 23.69 | 237 | 246 | 239 | 178 |
| 2 | 25.99 | 27.10 | 233 | 245 | 214 | 178 |
| 3 | 27.07 | 33.33 | 247 | 260 | 217 | 196 |
| 4 | 28.71 | 12.14 | 219 | 267 | 206 | 194 |
| 6 | 25.31 | 24.97 | 216 | 232 | 184 | 186 |
| 12 | 25.54 | 25.11 | 238 | 252 | 197 | 157 |
| 24 | 28.40 | 27.09 | 250 | 268 | 235 | 229 |
| 32 | 24.96 | 31.86 | 294 | 275 | 242 | 213 |
| 48 | 25.50 | 24.72 | 233 | 279 | 211 | 221 |
| 96 | 14.34 | 23.38 | 256 | 347 | 227 | 245 |
| 144 | 27.03 | 30.30 | 271 | 247 | 224 | 313 |
| Mean | 24.73 | 25.30 | 242.46 | 261.69 | 214.23 | 207.08 |
| Stdv. | 3.96 | 5.27 | 21.57 | 29.37 | 18.62 | 40.01 |
| % CV | 16.00 | 20.85 | 8.89 | 11.22 | 8.69 | 19.32 |

Formula I, 2-(2-(3,4-Difluorophenyl)ethyl)-1H-quinoline-4-1-yl N-(4'-trifluoromethylbiphenyl-4-ylmethyl)-acetamide bitartrate; is presented below and is described in WO 02/30904.

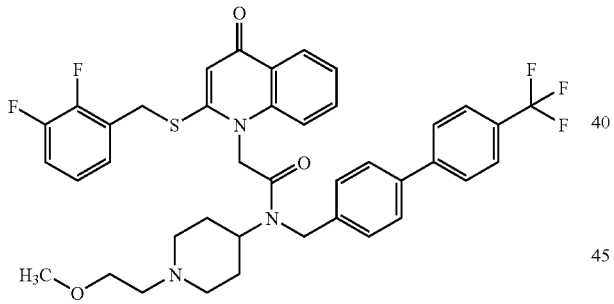

Formula I

Example 6

Comparison of Inhibition of Lp-PLA2 Activity Measured by the Auto PAF AH Assay and Low Throughput Radiometric Assay Plasma samples were evaluated from eight subjects who received 100 mg of a second Lp-PLA2 inhibitor during a clinical trial. The Lp-PLA2 inhibitor used in the study, 1-(N-(2-(Diethylamino)ethyl)-N-(4-(4-trifluoromethylphenyl)benzyl)-aminocarbonylmethyl)-2-(4-fluorobenzyl)thio-5,6-trimethylenepyrimidin-4-one bitartrate, is described below as Formula II and is described in WO 01/60805:

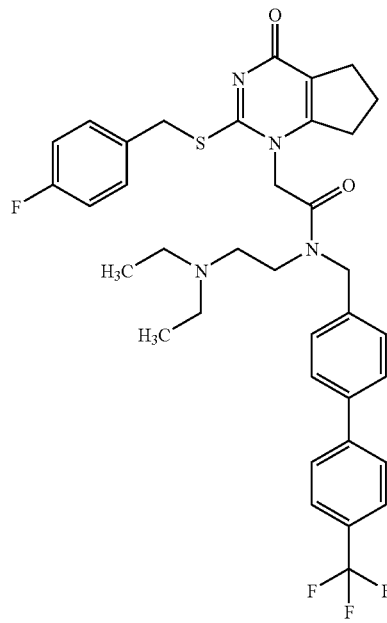

Formula II

Four of the eight subjects also received placebo on a different day.

Greater than 90% inhibition of Lp-PLA2 activity was observed using the low throughput radiometric assay for in vivo administration of the Lp-PLA2 inhibitor. However, no inhibition was measured with the Auto PAF AH assay (see Table 3). Lp-PLA2 activity values fluctuated for both the drug and placebo subjects as measured by Auto PAF AH assay apparently due to biological fluctuation.

TABLE 3

Inhibition of LP-PLA2 Activity as Measured by Auto PAF AH and Low Throughput Radiometric Assay.

| Timepoint (hr) | Drug #24 | Drug #25 | Drug #26 | Drug #27 | Drug #28 | Drug #29 | Drug #30 | Drug #31 |
|---|---|---|---|---|---|---|---|---|
| | LTP Radiometric Assay | | | | | | | |
| 0 | 20.48 | 20.11 | 25.74 | 24.56 | 23.95 | 30.95 | 25.58 | 23.13 |
| 0.5 | 6.74 | 10.08 | 1.85 | 16.77 | 4.43 | 22.16 | 10.97 | 8.05 |
| 1 | 1.03 | 2.14 | 1.89 | 5.21 | 3.25 | 4.28 | 7.63 | 3.93 |
| 2 | 0.88 | 0.77 | 1.62 | 2.45 | 1.97 | 2.13 | 6.10 | 1.10 |
| 3 | 0.82 | 1.20 | 1.83 | 1.74 | 2.25 | 2.07 | 2.43 | 0.92 |
| 4 | 1.48 | 1.21 | 1.85 | 1.28 | 2.43 | 2.20 | 2.00 | 1.13 |
| 6 | 1.45 | 1.22 | 1.67 | 1.74 | 3.25 | 2.66 | 2.74 | 1.20 |
| 12 | 2.98 | 3.06 | 4.20 | 3.99 | 5.34 | 7.20 | 5.43 | 3.37 |
| 24 | 5.59 | 5.99 | 7.18 | 7.06 | 8.30 | 15.24 | 8.94 | 5.23 |
| 32 | 8.24 | 5.44 | 20.40 | 8.95 | 7.94 | 32.93 | 10.40 | 7.39 |
| 48 | 10.06 | 7.62 | 20.18 | 13.29 | 11.24 | 27.30 | 13.81 | 8.56 |

TABLE 3-continued

Inhibition of LP-PLA2 Activity as Measured by Auto PAF AH and Low Throughput Radiometric Assay.

| Timepoint (hr) | Drug #24 | Drug #25 | Drug #26 | Drug #27 | Drug #28 | Drug #29 | Drug #30 | Drug #31 |
|---|---|---|---|---|---|---|---|---|
| 72 | 14.77 | 11.81 | 13.25 | 13.41 | 13.69 | 29.10 | 18.31 | 12.21 |
| 96 | 16.18 | 14.58 | 14.79 | 16.19 | 15.59 | 27.66 | 19.75 | 15.46 |
| Auto PAF AH Assay | | | | | | | | |
| 0 | 370 | 370 | 370 | 370 | 370 | 370 | 370 | 370 |
| 0.5 | 352 | 352 | 352 | 352 | 352 | 352 | 352 | 352 |
| 1 | 613 | 613 | 613 | 613 | 613 | 613 | 613 | 613 |
| 2 | 356 | 356 | 356 | 356 | 356 | 356 | 356 | 356 |
| 3 | 373 | 373 | 373 | 373 | 373 | 373 | 373 | 373 |
| 4 | 360 | 360 | 360 | 360 | 360 | 360 | 360 | 360 |
| 6 | 323 | 323 | 323 | 323 | 323 | 323 | 323 | 323 |
| 12 | 369 | 369 | 369 | 369 | 369 | 369 | 369 | 369 |
| 24 | 375 | 375 | 375 | 375 | 375 | 375 | 375 | 375 |
| 32 | 416 | 416 | 416 | 416 | 416 | 416 | 416 | 416 |
| 48 | 365 | 365 | 365 | 365 | 365 | 365 | 365 | 365 |
| 72 | 435 | 435 | 435 | 435 | 435 | 435 | 435 | 435 |
| 96 | 445 | 445 | 445 | 445 | 445 | 445 | 445 | 445 |

Example 7

Substrate Specificity Testing

A manual colorimetric Lp-PLA2 activity assay was developed using the substrate 1-myristoyl-2-(p-nitrophenylsuccinyl) phosphatidylcholine manufactured by Azwell (Osaka, Japan). This assay is a corresponding microtiter-plate version of the Auto PAF AH Assay compatible with a spectrophotometric plate reader. This manual assay was used to evaluate the physical properties of the substrate. Presented here are data on substrate specificity.

Materials
R1: 200 mM HEPES, 200 mM NaCl, 5 mM EDTA, 10 mM CHAPS, 10 mM Sodium 1-nonanesulfonate, pH 7.6, Store at 4° C.
R2A: 20 mM citric acid monohydrate, 10 mM sodium 1-nonanesulfonate, pH 4.5,
R2B: 1-myristoyl-2-(4-nitrophenylsuccinyl) phosphatidylcholine, 90 mM
p-nitrophenol: Sigma-Aldrich Chemical Co., St. Louis, Mo. (Cat #1048-25G)
Ethanol: Sigma-Aldrich Chemical Co., St. Louis, Mo. (Cat #7023)
Methanol: VWR International, West Chester, Pa. (Cat # EM-MX0482-6)

Reagent Preparation
R2: Mix R2A and R2B in ratio of 10:1. Store at 4° C. for no longer than two weeks before use.
p-Nitrophenol standards: Make 1M of 4-nitrophenol solution in Methanol. Dilute 100 µL, 75 µL, 50 µL, 25 µL, 10 µL, 5 µL of the 1M solution in 1 mL of Methanol to make 100, 75, 50, 25, 10, and 5 nmol/µL stock solution respectively. Make working solution for each standard by diluting 100 µL of stock solution into 900 µL of methanol (1:10 dilution). Store both stock and working solution at 4° C.

Assay Procedure
1. Set temperature of the plate reader (SPECTRAmax® PLUS$^{384}$ UV/VIS Microplate Spectrophotometer, Molecular Devices, Sunnyvale, Calif.) at 21° C.
2. Add 120 µL of R1 into each well in a 96-well flat-bottom assay plate (Costar 3595, Corning, Inc., Corning, N.Y.) using a multi-channel pipettor.
3. Add 10 µL of p-nitrophenol standard working solution into each of the duplicate wells in Column 1 and 2. Use 7 standard points for generating a standard curve: 0, 5, 10, 25, 50, 75, 100 nmol/well. Leave well 1H and 2H for blank controls.
4. Add 5 µL of plasma individually into each well. Use duplicate for each sample. Set up blank controls by adding 5 µL of ddH$_2$O instead of plasma into well 1H and 2H. Mix the plate well by hand.
5. Incubate the plate at 37° C. for 5 minutes.
6. Cool the plate at 21° C. in the plate reader for 5 minutes.
7. Take the plate out from the plate reader. Add 40 µL of R2 into each well using a multi-channel pipettor, changing tips after each addition. Time the start of R2 addition.
8. Add 2 µL of ethanol into each well using a multi-channel pipettor, changing tips after each addition. The purpose of this step is to rid of all the air bubbles generated in wells. The duration between first R2 addition and plate reading in Step #9 is 4 minutes.
9. Read the plate at 405 nm for 20 minutes with a 2-minute interval. Include a 2-minute auto-mixing before reading the plate.

Activity Calculation
1. Generate a standard curve by plotting average OD values at 0 and 20 minutes (OD$_{0min}$ and OD$_{20min}$) for the 7 standards vs. p-nitrophenol (nmol/well). Calculate the slope of the standard curve.
2. Calculate ΔOD values for each blank well between 2 and 4 minutes (OD$_{4min}$-OD 2 min) and average the two ΔOD values for the blanks
3. For each sample well, calculate ΔOD values between 2 and 4 minutes and then Lp-PLA2 activity (nmol/min/ml)= (ΔOD$_{sample}$−ΔOD$_{blank}$)÷slope (OD/nmol)÷0.005 ml÷2 minutes.
4. Calculate an average activity value for duplicate sample wells.

Results

Substrate specificity against Lp-PLA2 was assayed by using two Lp-PLA2 inhibitor compounds; Formula II, which is described in Example 6, and Formula III, which is presented below:

Formula III

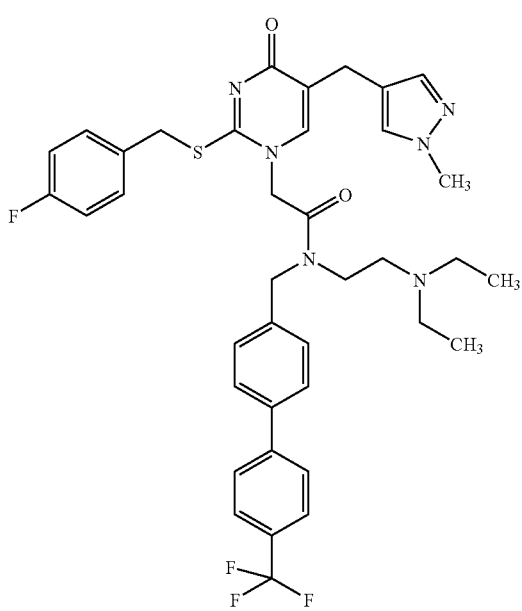

Formula III or 1-(N-(2-(Diethylamino)ethyl)-N-(4-(4-trifluoromethylphenyl)benzyl)aminocarbonylmethyl)-2-(4-fluorobenzyl)thio-5-(1-methylpyrazol-4-ylmethyl)pyrimidin-4-one is described in WO 00/66567.

Plasma samples from four healthy patients were incubated in vitro with increasing amount of Formula III. For addition of the inhibitor solution to the reaction mixtures, a 100 mM stock solution was prepared in DMSO. A series of 1:10 working dilutions were prepared in DMSO to give concentrations which ranged between 10 mM and 0.01 nM. One microliter aliquots of each working dilution were added in each reaction. The final concentrations of Lp-PLA2 inhibitor were (in nM) 60,000, 6,000, 600, 60, 6, 0.6, 0.06, 0.006, 0.0006, 0.00006 and 0.

All four plasma demonstrated decreasing Lp-PLA2 activity as shown in Table 4. Inhibition achieved by Formula III in all four samples reached over 90%, comparable to the natural Lp-PLA2 substrate PAF used in the radiometric activity assay. Formula II also showed over 90% inhibition of the substrate hydrolysis when incubated in vitro in the same four plasma samples.

TABLE 4

In Vitro Inhibition of Lp-PLA2 Activity by Formula III in Four Plasma Samples

| Drug (nM) | Activity (nmol/min/mL) | | | | % Inhibition | | | |
|---|---|---|---|---|---|---|---|---|
| | #3 | #7 | #8 | #10 | #3 | #7 | #8 | #10 |
| 600 | 22.65 | 10.50 | 9.67 | 10.91 | 88.50 | 92.75 | 90.37 | 93.78 |
| 60 | 16.25 | 12.64 | 0.14 | 14.17 | 91.75 | 91.28 | 99.86 | 91.92 |
| 6 | 48.61 | 31.39 | 21.81 | 35.97 | 75.32 | 78.33 | 78.29 | 79.49 |
| 0.6 | 102.78 | 78.61 | 50.69 | 83.89 | 47.81 | 45.73 | 49.52 | 52.18 |
| 0.06 | 167.36 | 119.17 | 83.33 | 148.89 | 15.02 | 17.74 | 17.02 | 15.12 |
| 0.006 | 162.22 | 138.06 | 95.42 | 178.61 | 17.63 | 4.70 | 4.98 | −1.82 |
| 0.0006 | 200.97 | 142.36 | 86.67 | 179.17 | −2.05 | 1.73 | 13.70 | −2.14 |
| 0 | 196.94 | 144.86 | 100.42 | 175.42 | 0 | 0 | 0 | 0 |

The assay buffer used in above experiments has high content of detergent (7.5 mM CHAPS and 10 mM Sodium 1-nonanesulfonate). When detergent was eliminated from the assay, Formula III only inhibited about 65% of hydrolysis activity in plasma sample #10. When detergent was added in the parallel experiment inhibition of more than 95% was reached. Therefore, it appears that this substrate is specific to Lp-PLA2 only when it is assayed in the presence of buffer comprising detergent, as shown in Table 5.

TABLE 5

Effect of Detergent on Substrate Specificity

| | % Inhibition | |
|---|---|---|
| Drug (nM) | with detergent | without detergent |
| 60000 | 96.01 | 68.01 |
| 6000 | 95.68 | 62.73 |
| 600 | 95.06 | 61.30 |
| 60 | 87.94 | 55.03 |
| 6 | 76.92 | 54.97 |
| 0.6 | 69.90 | 46.52 |
| 0.06 | 48.58 | 26.96 |
| 0.006 | 24.22 | 26.65 |
| 0.0006 | 19.18 | 19.88 |
| 0.00006 | 10.68 | 7.20 |
| 0 | 0 | 0 |

Example 8

Modified Drug Sensitive Colorimetric Assay for Measurement of Lp-PLA2 Activity

For the Auto PAF AH assay, plasma samples are diluted about 160-fold and the substrate is used at a concentration higher than its Km. It appears that when the concentration of substrate is higher than its Km the substrate competes with drug bound to Lp-PLA2 and promotes drug dissociation from the enzyme. For instance, the substrate concentration used in the Auto PAF AH assay is 1100 μM, which is more than 5 times higher than its Km (Km is about 200 μM when plasma is used as the enzyme source and assayed by Auto PAF AH protocol, see Example 1). Pre-incubation of plasma with buffer R1 in Auto PAF AH assay also appears to promote drug dissociation before the start of assay reaction. Therefore, the assay of the present invention was modified by using higher plasma sample volumes and lower substrate concentrations compared with the Auto PAF AH assay. Additionally, the pre-incubation step of plasma with R1 prior to substrate addition was eliminated. Moreover, elimination of buffer R2A increased reaction rates, which in turn enabled the use of lower substrate concentrations and a shorter assay incubation time during which drug dissociates compared with the Auto PAF AH assay Materials
R1: 200 mM HEPES, 200 mM NaCl, 5 mM EDTA, 10 mM CHAPS, 10 mM sodium 1-nonanesulfonate, pH 7.6
R2B: 90 mM 1-myristoyl-2-(4-nitrophenylsuccinyl) phosphatidylcholine
p-nitrophenol: Sigma-Aldrich Chemical Co., St. Louis, Mo. (Cat #1048-25G)

Reagent Preparation

Assay buffer: Mix R2B and R1 in a ratio of 0.66 µL to 110 µL. Store on ice or at 4° C. Prepare immediately before use.

p-Nitrophenol standards: Prepare 1M p-nitrophenol in methanol. Dilute 100, 75, 50, 25, 10 and 5 µL of 1M p-nitrophenol to 1 mL in methanol to prepare 100, 75, 50, 25, 10 and 5 nmol/µL stock solutions, respectively. Prepare working solutions for each standard by diluting 40 µL of stock solution into 960 µL of methanol (1:25 dilution). Store stock and working solutions at 4° C.

Assay Procedure

1. Add 120 µL of assay buffer to each well in a 96-well V-bottom plate (Costar 3897, Corning, Inc., Corning, N.Y.) using a multi-channel pipettor or robot.
2. Add 25 µL of p-nitrophenol standard working solution into duplicate wells in columns 1 and 2 on another 96-well flat-bottom plate (Costar 9017, Corning, Inc., Corning, N.Y.). Use 7 standard points for generating a standard curve: 0, 5, 10, 25, 50, 75, 100 nmol/well. Add 25 µL of PBS into well 1H and 2H for blank controls.
3. Briefly centrifuge plasma to spin down fibrin clot/particles. Add 25 µL of plasma per well in columns 3-12 on the same flat-bottom plate containing p-nitrophenol standards. Use duplicates for each sample.
4. Use a multi-channel pipettor or a robot to transfer 110 µL of assay buffer from the V-bottom plate to the flat-bottom assay plate containing plasma samples and p-nitrophenol standards. A Zymark RapidPlate (Caliper Life Sciences, Hopkinton, Mass.) can perform this step without generating bubbles in the wells. Other transfer methods may generate bubbles due to the high detergent content of R1. A small volume of ethanol can be used to eliminate air bubbles.
5. Immediately place the assay plate onto the plate reader (SPECTRAmax® PLUS[384] UV/VIS Microplate Spectrophotometer, Molecular Devices, Sunnyvale Calif.) and auto-mix for 15 seconds.
6. Read the plate at 405 nm for 10 minutes at 15-second intervals at room temperature. The duration between the start of enzymatic reaction (addition of assay buffer to the assay plate) and completion of the first absorbance reading is 1 minute.

The assay may be performed at room temperature. More stringent temperature control may be required if room temperature fluctuates within or between labs.

Activity Calculation

1. Generate a standard curve by plotting average OD values at 0 and 10 minutes ($OD_{0min}$ and $OD_{10min}$) for the seven standards vs. p-nitrophenol (nmol/well). Calculate the slope of the standard curve.
2. Calculate Change in ($\Delta OD$) values for each blank well between 1 and 3 minutes ($OD_{3min}-OD_{imm}$) and average the two $\Delta OD$ values for the blanks
3. For each sample well, calculate $\Delta OD$ values between 1 and 3 minutes and then Lp-PLA2 activity (nmol/min/ml)= ($\Delta OD_{sample}-\Delta OD_{blank}$)÷slope (OD/nmol)÷0.025 ml÷2 minutes.
4. Calculate an average activity value for duplicate sample wells.

Example 9

Comparison of Radiometric Measurement Versus Modified Drug Sensitive Colorimetric Measurement of Lp-PLA2 Activity in the Presence of Lp-PLA2 Inhibitor Lp-PLA2 activity from blood plasma samples obtained from a healthy human subject administered an Lp-PLA2 inhibitor was measured using the high throughput radiometric assay described in Example 2 and the methods of Example 8 with the following minor changes. The volume of plasma used per well was 25 µL. Substrate concentration was 1125 µM and, 2 µL of substrate solution R2B was mixed in 40 µL of R2A before further mixing with 95 µL of R1 to make the assay buffer. Blood plasma samples were collected at five timepoints after dosing (0.5, 1.0, 6.0, 48 and 96 hours post dosing). Both radiometric and colorimetric assays were used to determine Lp-PLA2 activity as well as percent inhibition in each sample as shown in Table 6. As shown in Table 6, percent inhibition of Lp-PLA2 activity as measured by a radiometric assay showed peak inhibition as about 94% one hour after dosing while a modified drug sensitive colorimetric assay showed peak inhibition at the 6-hour timepoint with about 64% inhibition in activity. These data demonstrate that both methods can be used to measure the inhibition of Lp-PLA2 activity in samples obtained from an animal that has been administered an Lp-PLA2 inhibitor. Blood samples from humans are considered to be essentially free of Lp-PLA2 inhibitor 96 hours post dosing.

TABLE 6

Comparison of Lp-PLA2 Activity as Measured Using Radiometric versus Modified Drug Sensitive Colorimetric Assay

| Time Point (hour) | Radiometric Assay | | Colorimetric Assay | |
|---|---|---|---|---|
| | Activity (nmol/min/mL) | % Inhibition (96 hr-100%) | Activity (milliOD/min) | % Inhibition (96 hr-100%) |
| 0.5 | 28.02 | 47.00 | 34.47 | 36.55 |
| 1 | 3.19 | 93.97 | 22.98 | 57.70 |
| 6 | 10.14 | 80.83 | 19.8 | 63.56 |
| 48 | 44.52 | 15.80 | 33.76 | 37.86 |
| 96 | 52.87 | 0 | 54.33 | 0 |

Example 10

Testing of Plasma Samples from a Clinical Study for Lp-PLA2 Inhibition

Four human subjects recruited in a clinical trial of a novel Lp-PLA2 inhibitor, Formula I (see Example 5) received different doses of the drug. Drug dose for Subject #13, #36, #24, and #41 was 80 mg, 120 mg, 180 mg, and 240 mg, respectively. Plasma was collected at 0, 0.5, 1, and 3 hours after drug administration. Lp-PLA2 activity of these plasma samples was assayed by the low throughput radiometric assay described in Example 4, the Auto PAF AH assay, described in Example 1, and modified drug-sensitive colorimetric assay, which is described in this Example 8. While the radiometric activity assay indicated >90% inhibition of Lp-PLA2 activity 3 hours after dosing in all four subjects, the Auto PAF AH assay failed to indicate drug inhibition. However, a modified drug-sensitive colorimetric assay of Example 8 indicated 85-90% drug inhibition as shown in Table 7.

TABLE 7

Percent Inhibition of Lp-PLA2 Activity in Plasma Samples from Subjects Administered Lp-PLA2 Inhibitor

| Time | Radiometric Assay | | | | Auto PAF AH Assay Pt. No. | | | | Drug-Sensitive Colorimetric Assay | | | |
|---|---|---|---|---|---|---|---|---|---|---|---|---|
| (hr) | 13 | 36 | 24 | 41 | 13 | 36 | 24 | 41 | 13 | 36 | 24 | 41 |
| 0 | 0 | 0 | 0 | 0 | 0 | 0 | 0 | 0 | 0 | 0 | 0 | 0 |
| 0.5 | 46.12 | 45.06 | 9.58 | 26.68 | 5.60 | 8.38 | 6.26 | 8.60 | 32.82 | 45.62 | 6.73 | 18.41 |
| 1 | 81.79 | 91.46 | 90.98 | 88.27 | 9.98 | 14.03 | 11.53 | 14.55 | 73.08 | 84.97 | 86.26 | 77.78 |
| 3 | 93.74 | 94.36 | 97.32 | 96.02 | 7.11 | 10.93 | 10.36 | 15.70 | 85.64 | 85.3 | 89.15 | 88.37 |

Similarly, both the radiometric assay and modified drug-sensitive colorimetric assay showed a measured time-dependent effect on Lp-PLA2 activity after dosing with Lp-PLA2 inhibitor as shown in Table 8. Little effect on Lp-PLA2 activity was observed using the Auto PAF AH assay as shown in Table 8.

TABLE 8

Lp-PLA2 Activity in Plasma Samples from Subjects Administered Lp-PLA2 Inhibitor

Lp-PLA2 Activity (nmol/min/mL)

| Time | Radiometric Assay | | | | Auto PAF AH Assay Pt. No. | | | | Drug-Sensitive Colorimetric Assay | | | |
|---|---|---|---|---|---|---|---|---|---|---|---|---|
| (hr) | 13 | 36 | 24 | 41 | 13 | 36 | 24 | 41 | 13 | 36 | 24 | 41 |
| 0 | 27.3 | 26.94 | 39.13 | 46.97 | 330.50 | 605.00 | 511.50 | 274.50 | 96.9 | 83.84 | 177.63 | 176.2 |
| 0.5 | 14.71 | 14.8 | 35.38 | 34.44 | 312.00 | 553.00 | 479.50 | 251.50 | 65.1 | 45.59 | 165.67 | 143.76 |
| 1 | 4.97 | 2.3 | 3.53 | 5.51 | 297.50 | 517.00 | 452.50 | 236.00 | 26.08 | 12.61 | 24.41 | 39.14 |
| 3 | 1.71 | 1.52 | 1.05 | 1.87 | 307.00 | 510.00 | 458.50 | 244.50 | 13.92 | 12.33 | 19.27 | 20.49 |

Although the activity values generated from radiometric and modified drug-sensitive colorimetric assay are different, correlation between the two assays is r=0.975 for these 16 clinical plasma samples. Therefore, modified drug-sensitive colorimetric assays, described herein, although using the same substrate as the Auto PAF AH assay, demonstrated ability to detect in vivo drug inhibition of Lp-PLA2 in drug-treated human subjects, while the Auto PAF AH assay did not.

Example 11

Testing of Additional Plasma Samples from a Clinical Study for Lp-PLA2 Inhibition Plasma samples were collected from ten subjects in a clinical trial for the Lp-PLA2 inhibitor of Formula I. Subjects #109, #114, #115, #142 and #145 received 50 mg of Formula I while subjects #118, #119, #121, #123 and #124 received 120 mg of the compound. Lp-PLA2 activity of these plasma samples were assayed by the high throughput radiometric assay as described in Example 4, the Auto PAF AH assay as described in Example 1, and modified drug-sensitive colorimetric assay as described in Example 8. Consistently, the Auto PAF AH assay failed to measure drug inhibition of Lp-PLA2 activity in these samples with maximal inhibition of 29% detected in subject #123. However, a modified drug-sensitive colorimetric assay of Example 8 indicated comparable drug inhibition with radiometric assay in all subjects. Inhibition values for the radiometric assay and a modified, drug-sensitive colorimetric assay agreed within 15% for all but four time (#114/12 hr, #115/12 hr, #142/0.5 hr and #142/12 hr) as shown in Table 9.

TABLE 9

Lp-PLA2 Activity and Percent Inhibition by Subject and Assay

| Subject | Time (hr) | Lp-PLA2 Activity (nmol/min/mL) | | | % Inhibition | | |
|---|---|---|---|---|---|---|---|
| | | Radiometric | Auto PAF AH | Drug-Sensitive Colorimetric | Radiometric | Auto PAF AH | Drug-Sensitive Colorimetric |
| #109 | 0 | 140.47 | 703.50 | 193.21 | 0.00 | 0.00 | 0.00 |
| | 0.5 | 104.52 | 647.00 | 141.14 | 25.59 | 8.03 | 26.95 |

TABLE 9-continued

Lp-PLA2 Activity and Percent Inhibition by Subject and Assay

| Subject | Time (hr) | Lp-PLA2 Activity (nmol/min/mL) | | | % Inhibition | | |
|---|---|---|---|---|---|---|---|
| | | Radiometric | Auto PAF AH | Drug-Sensitive Colorimetric | Radiometric | Auto PAF AH | Drug-Sensitive Colorimetric |
| | 1 | 26.80 | 605.00 | 39.10 | 80.92 | 14.00 | 79.76 |
| | 2 | 14.51 | 559.50 | 30.57 | 89.67 | 20.47 | 84.18 |
| | 3 | 18.06 | 602.50 | 35.03 | 87.14 | 14.36 | 81.87 |
| | 4 | 20.76 | 629.50 | 33.46 | 85.22 | 10.52 | 82.68 |
| | 5 | 19.57 | 651.50 | 31.77 | 86.07 | 7.39 | 83.55 |
| | 6 | 21.78 | 642.00 | 66.08 | 84.49 | 8.74 | 65.80 |
| | 9 | 32.01 | 571.50 | 49.86 | 77.21 | 18.76 | 74.19 |
| | 12 | 35.85 | 571.50 | 76.84 | 74.48 | 18.76 | 60.23 |
| #114 | 0 | 84.01 | 512.00 | 127.01 | 0.00 | 0.00 | 0.00 |
| | 0.5 | 65.24 | 456.50 | 89.99 | 22.34 | 10.84 | 29.15 |
| | 1 | 18.68 | 414.50 | 24.96 | 77.76 | 19.04 | 80.35 |
| | 2 | 14.34 | 406.50 | 21.22 | 82.93 | 20.61 | 83.29 |
| | 3 | 12.24 | 435.00 | 18.66 | 85.43 | 15.04 | 85.31 |
| | 4 | 13.50 | 409.00 | 18.15 | 83.93 | 20.12 | 85.71 |
| | 5 | 14.14 | 385.00 | 16.58 | 83.17 | 24.80 | 86.94 |
| | 6 | 16.10 | 388.50 | 21.01 | 80.84 | 24.12 | 83.46 |
| | 9 | 24.73 | 445.50 | 37.35 | 70.56 | 12.99 | 70.59 |
| | 12 | 28.82 | 409.50 | 111.00 | 65.69 | 20.02 | 12.60 |
| #115 | 0 | 60.58 | 310.00 | 83.99 | 0.00 | 0.00 | 0.00 |
| | 0.5 | 50.18 | 308.00 | 69.79 | 17.17 | 0.65 | 16.91 |
| | 1 | 10.60 | 242.00 | 22.46 | 82.50 | 21.94 | 73.26 |
| | 2 | 10.00 | 282.00 | 16.31 | 83.49 | 9.03 | 80.58 |
| | 3 | 13.03 | 287.50 | 21.31 | 78.49 | 7.26 | 74.62 |
| | 4 | 14.37 | 309.00 | 21.77 | 76.28 | 0.32 | 74.08 |
| | 5 | 13.63 | 279.50 | 15.83 | 77.50 | 9.84 | 81.16 |
| | 6 | 15.96 | 306.50 | 25.84 | 73.65 | 1.13 | 69.24 |
| | 9 | 25.91 | 289.50 | 36.27 | 57.23 | 6.61 | 56.82 |
| | 12 | 26.92 | 336.00 | 53.72 | 55.56 | −8.39 | 36.04 |
| #118 | 0 | 101.65 | 382.50 | 102.59 | 0.00 | 0.00 | 0.00 |
| | 0.5 | 35.83 | 323.50 | 31.08 | 64.75 | 15.42 | 69.70 |
| | 1 | 16.73 | 334.00 | 19.69 | 83.54 | 12.68 | 80.81 |
| | 2 | 13.70 | 313.50 | 19.69 | 86.52 | 18.04 | 80.81 |
| | 3 | 14.09 | 335.00 | 13.17 | 86.14 | 12.42 | 87.16 |
| | 4 | 14.00 | 346.50 | 7.30 | 86.23 | 9.41 | 92.88 |
| | 5 | 14.05 | 353.50 | 22.94 | 86.18 | 7.58 | 77.64 |
| | 6 | 15.68 | 330.00 | 20.65 | 84.57 | 13.73 | 79.87 |
| | 9 | 21.11 | 338.00 | 27.16 | 79.23 | 11.63 | 73.52 |
| | 12 | 24.22 | 355.50 | 38.74 | 76.17 | 7.06 | 62.24 |
| #119 | 0 | 141.40 | 736.00 | 180.59 | 0.00 | 0.00 | 0.00 |
| | 0.5 | 25.97 | 596.50 | 20.14 | 81.63 | 18.95 | 88.89 |
| | 1 | 16.04 | 568.00 | 23.29 | 88.66 | 22.83 | 87.10 |
| | 2 | 13.50 | 579.00 | 19.54 | 90.45 | 21.33 | 89.18 |
| | 3 | 12.80 | 616.50 | 20.61 | 90.95 | 16.24 | 88.59 |
| | 4 | 12.85 | 597.50 | 21.27 | 90.91 | 18.82 | 88.22 |
| | 5 | 11.69 | 748.00 | 21.36 | 91.73 | −1.63 | 88.17 |
| | 6 | 11.41 | 714.00 | 21.39 | 91.93 | 2.99 | 88.16 |
| | 9 | 18.51 | 578.50 | 27.87 | 86.91 | 21.40 | 84.57 |
| | 12 | 21.27 | 607.50 | 38.46 | 84.96 | 17.46 | 78.70 |
| #121 | 0 | 97.09 | 440.50 | 134.39 | 0.00 | 0.00 | 0.00 |
| | 0.5 | 16.07 | 402.00 | 19.87 | 83.45 | 8.74 | 85.22 |
| | 1 | 10.00 | 401.00 | 14.99 | 89.70 | 8.97 | 88.85 |
| | 2 | 10.00 | 402.50 | 12.22 | 89.70 | 8.63 | 90.90 |
| | 3 | 10.00 | 414.50 | 15.08 | 89.70 | 5.90 | 88.78 |
| | 4 | 10.00 | 389.50 | 16.18 | 89.70 | 11.58 | 87.96 |
| | 5 | 10.00 | 416.00 | 18.14 | 89.70 | 5.56 | 86.50 |
| | 6 | 10.26 | 412.00 | 18.74 | 89.43 | 6.47 | 86.06 |
| | 9 | 14.41 | 428.00 | 26.18 | 85.16 | 2.84 | 80.52 |
| | 12 | 16.97 | 456.00 | 35.87 | 82.52 | −3.52 | 73.31 |
| #123 | 0 | 72.11 | 454.00 | 116.90 | 0.00 | 0.00 | 0.00 |
| | 0.5 | 39.68 | 410.50 | 63.95 | 44.97 | 9.58 | 45.29 |
| | 1 | 19.83 | 402.50 | 30.22 | 72.50 | 11.34 | 74.15 |
| | 2 | 19.42 | 369.50 | 29.51 | 73.07 | 18.61 | 74.76 |
| | 3 | 21.08 | 387.50 | 30.49 | 70.77 | 14.65 | 73.92 |
| | 4 | 19.51 | 406.50 | 29.42 | 72.94 | 10.46 | 74.84 |
| | 5 | 20.24 | 428.50 | 35.46 | 71.93 | 5.62 | 69.67 |
| | 6 | 19.66 | 393.00 | 39.29 | 72.74 | 13.44 | 66.39 |
| | 9 | 32.48 | 343.00 | 50.81 | 54.96 | 24.45 | 56.54 |
| | 12 | 34.26 | 324.00 | 61.16 | 52.49 | 28.63 | 47.69 |
| #124 | 0 | 87.96 | 465.50 | 109.88 | 0.00 | 0.00 | 0.00 |
| | 0.5 | 58.09 | 434.50 | 64.40 | 33.96 | 6.66 | 41.39 |
| | 1 | 12.39 | 429.50 | 18.74 | 85.91 | 7.73 | 82.95 |

TABLE 9-continued

Lp-PLA2 Activity and Percent Inhibition by Subject and Assay

| Subject | Time (hr) | Lp-PLA2 Activity (nmol/min/mL) | | | % Inhibition | | |
|---|---|---|---|---|---|---|---|
| | | Radiometric | Auto PAF AH | Drug-Sensitive Colorimetric | Radiometric | Auto PAF AH | Drug-Sensitive Colorimetric |
| | 2 | 10.00 | 367.50 | 10.11 | 88.63 | 21.05 | 90.80 |
| | 3 | 10.00 | 362.50 | 11.51 | 88.63 | 22.13 | 89.53 |
| | 4 | 10.00 | 403.00 | 11.21 | 88.63 | 13.43 | 89.80 |
| | 5 | 10.00 | 377.00 | 12.22 | 88.63 | 19.01 | 88.88 |
| | 6 | 10.00 | 366.00 | 17.01 | 88.63 | 21.37 | 84.52 |
| | 9 | 11.21 | 387.00 | 21.03 | 87.26 | 16.86 | 80.86 |
| | 12 | 15.69 | 355.00 | 30.70 | 82.16 | 23.74 | 72.06 |
| #142 | 0 | 77.38 | 368.50 | 100.48 | 0.00 | 0.00 | 0.00 |
| | 0.5 | 78.40 | 393.00 | 81.70 | −1.32 | −6.65 | 18.69 |
| | 1 | 30.87 | 340.50 | 37.07 | 60.11 | 7.60 | 63.11 |
| | 2 | 14.73 | 348.00 | 27.05 | 80.96 | 5.56 | 73.08 |
| | 3 | 12.41 | 348.00 | 22.64 | 83.96 | 5.56 | 77.47 |
| | 4 | 11.47 | 338.50 | 19.97 | 85.18 | 8.14 | 80.12 |
| | 5 | 10.66 | 336.50 | 18.35 | 86.22 | 8.68 | 81.74 |
| | 6 | 12.93 | 325.00 | 25.12 | 83.29 | 11.80 | 75.00 |
| | 9 | 22.03 | 312.00 | 38.84 | 71.53 | 15.33 | 61.34 |
| | 12 | 21.96 | 307.00 | 44.60 | 71.62 | 16.69 | 55.61 |
| #145 | 0 | 63.55 | 305.00 | 88.69 | 0.00 | 0.00 | 0.00 |
| | 0.5 | 22.46 | 272.50 | 32.96 | 64.66 | 10.66 | 62.84 |
| | 1 | 15.85 | 271.00 | 17.15 | 75.06 | 11.15 | 80.66 |
| | 2 | 14.45 | 271.50 | 21.07 | 77.26 | 10.98 | 76.24 |
| | 3 | 11.99 | 277.50 | 20.89 | 81.13 | 9.02 | 76.45 |
| | 4 | 10.02 | 256.50 | 19.02 | 84.23 | 15.90 | 78.55 |
| | 5 | 10.14 | 273.50 | 20.74 | 84.04 | 10.33 | 76.62 |
| | 6 | 11.33 | 273.50 | 23.71 | 82.17 | 10.33 | 73.27 |
| | 9 | 17.58 | 286.00 | 33.36 | 72.34 | 6.23 | 62.39 |
| | 12 | 20.83 | 261.50 | 34.83 | 67.22 | 14.26 | 60.73 |

Correlation of r=0.95 was obtained between a modified, drug-sensitive colorimetric assay and the radiometric assay for the 100 samples analyzed in this study. The Auto PAF AH assay showed poor correlation with radiometric assay in these drug dosed samples (r=0.31).

Example 12

Assay Dynamic Range

Instrument Low Limit of Quantitation

Twenty-five microliters of PBS were added into 110 μL of R1 containing 0.67 μL of R2B. Sixteen replicates were prepared and randomly placed in wells across a microtiter plate. Absorbance at 405 nm was obtained and standard deviation calculated between replicates. Six times standard deviation (6×SD) was defined as the lower limit of quantitation for the microtiter plate reader (SPECTRAmax® PLUS[384] UV/VIS Microplate Spectrophotometer, Molecular Devices, Sunnyvale, Calif.). The average OD reading from 16 replicates was 0.0437 with a standard deviation of 0.0009. The lower limit of quantitation for the microtiter plate reader was defined as 6×0.0009 or a change of 0.0054 OD units during assay incubation.

Linear Detection Range of p-Nitrophenol

Serial dilutions of p-nitrophenol were prepared in methanol. Twenty-five microliters of p-nitrophenol at each concentration were added to 110 μl R1 (without R2B) in a microtiter plate. Absorbance values at 405 nm were linear between 0.05 to 125 nmol of p-nitrophenol (r=0.996). However, the blank corrected absorbance of the 0.05 nmol p-nitrophenol sample was only 0.00415, which is below the microtiter plate reader's lower limit of quantitation of 0.0054 OD as defined above. Therefore, the linear detection range of p-nitrophenol is set between 0.1 and 125 nmol of p-nitrophenol per well.

Assay Dynamic Range

Assay dynamic range was defined by using both recombinant human Lp-PLA2 protein (hrLp-PLA2) generated in-house and Lp-PLA2 protein purified from human plasma in-house.

hrLp-PLA2 was serially diluted and 25 μL of each diluted hrLp-PLA2 were assayed by a modified drug-sensitive colorimetric assay (data shown in Table 10). The second least amount of hrLp-PLA2 assayed 206 ng/mL showed an activity of 1.5 nmol/min/mL. Such level of activity would only generate 0.075 nmol of p-nitrophenol in two minutes of substrate hydrolysis reaction in the current assay configuration. Therefore, it is lower than the linear detection range of the end product p-nitrophenol. hrLp-PLA2 greater than 13200 ng/mL showed plateau activity. The activity of hrLp-PLA2 between 412 to 13200 ng/mL demonstrated linearity with an R value of 0.997. Therefore, the dynamic range of this assay appears to be between 4.4 and 397 nmol/min/mL, although lower and upper limits could be further defined. (see Table 10).

TABLE 10

Activity of Recombinant Human Lp-PLA2 Protein by Modified Colorimetric Assay

| hrLp-PLA2 (ng/ml) | Activity (nmol/min/mL) |
|---|---|
| 0 | 0.0 |
| 103 | 0.6 |
| 206 | 1.5 |
| 412 | 4.4 |
| 825 | 12.0 |
| 1650 | 30.0 |

TABLE 10-continued

Activity of Recombinant Human Lp-PLA2 Protein by Modified Colorimetric Assay

| hrLp-PLA2 (ng/ml) | Activity (nmol/min/mL) |
|---|---|
| 3300 | 69.7 |
| 6600 | 169.0 |
| 13200 | 397.1 |
| 14666 | 413.7 | hLp-PLA2 purified from plasma was also serially diluted and 25 μL of each dilution were assayed by a modified drug-sensitive colorimetric assay (data shown in Table 11). The activity of purified hLp-PLA2 protein ranged between 6.25 to 1200 ng/mL demonstrated linearity with an R value of 0.97. Therefore, the dynamic range assessed using purified hLp-PLA2 appears to be between 2.47 and 363.60 nmol/min/mL, comparable to the one defined by hrLp-PLA2 (see Table 11). The relatively lower upper limit of the dynamic range determined by purified hLp-PLA2 may be resulted from interference factors possibly present in the purified product and/or introduced during purification process. Limited availability of such purified protein prevents further investigation.

TABLE 11

Activity of Purified Human Lp-PLA2 Enzyme by Modified Drug Sensitive Colorimetric Assay

| Purified hLp-PLA2 (ng/ml) | Activity (nmol/min/mL) |
|---|---|
| 0.00 | 0.00 |
| 1.56 | 0.65 |
| 3.13 | 1.37 |
| 6.25 | 2.47 |
| 12.50 | 5.06 |
| 25.00 | 11.37 |
| 50.00 | 25.68 |
| 75.00 | 37.83 |
| 100.00 | 54.34 |
| 200.00 | 119.34 |
| 400.00 | 212.95 |
| 600.00 | 273.60 |
| 800.00 | 324.85 |
| 1000.00 | 338.51 |
| 1200.00 | 363.60 |
| 1600.00 | 335.42 |

Example 13

Substrate Stability

Stability of the substrate in modified assay buffer (110 μL R1+0.67 μL R2B+25 μL PBS) was examined by monitoring absorbance changes every 15 minutes over 120 minutes at room temperature. Although absorbance increased slowly but consistently over 2 hours reflecting gradual substrate degradation, the change in absorbance was only 0.002 OD units per 15 minutes. Therefore, substrate degradation appears to be moderate over 2 hours under a modified assay conditions. Since the assay takes only 10 minutes to complete and activity is calculated based on a 2-minute reaction period, absorbance changes from substrate degradation are insignificant and can be blank-corrected.

Example 14

Effect of Pre-Incubation of Human Plasma with Buffer R1 on Drug-Sensitivity

In the Auto PAF AH assay, plasma is pre-incubated in buffer R1 at 37° C. for 5 minutes. This pre-incubation step may accelerate the dissociation of drug bound to Lp-PLA2 before the start of the reaction. To test whether accelerated dissociation occurs, a plasma sample from a human subject (#10) was incubated with increasing amount of Lp-PLA2 inhibitor at 37° C. for an hour. Twenty-five microliters of the in vitro Formular II drug-treated plasma was then pre-incubated with 100 μL R1 at room temperature for different times before running the assay for 10 minutes at room temperature after addition of 40 μL of R2 (final substrate concentration of 1100 μM). Pre-incubation of plasma with R1 decreased drug-inhibition especially at lower drug concentrations. The highest level of drug inhibition was obtained when R1 and R2 were premixed and added directly to plasma without pre-incubation, as shown in Table 12. Pre-incubation of plasma in R1 at 37° C. instead of room temperature further deteriorates drug inhibition.

TABLE 12

Effect of Preincubation of Plasma in Buffer R1 on Percent Inhibition of Lp-PLA2 Activity

| | Preincubation of Plasma in R1 Buffer Reaction Time (minutes) | | | |
|---|---|---|---|---|
| Drug (ng/mL) | 5 minutes | 2 minutes | 0 minutes | R1R2 premix |
| 0 | 0.00 | 0.00 | 0.00 | 0.00 |
| 2 | -2.33 | 3.94 | 10.76 | 15.10 |
| 5 | 2.39 | 4.83 | 17.18 | 25.76 |
| 10 | 9.35 | 10.03 | 18.97 | 27.17 |
| 30 | 35.14 | 42.02 | 45.19 | 53.92 |
| 60 | 39.97 | 39.17 | 49.00 | 57.64 |
| 90 | 72.26 | 72.58 | 76.61 | 77.69 |

Example 15

Effect of Substrate Concentration on Drug-Sensitivity

The substrate concentration is 1100 μM in the Auto PAF AH assay, which is more than 5 times higher than its Km (Km=200 μM when plasma is used as the enzyme source and assayed by Auto PAF AH protocol). High substrate concentrations may compete with drug binding to Lp-PLA2. To test this possibility, 25 μL of in vitro Lp-PLA2 inhibitor Formular II treated human plasma samples were added to premixed R1 (100 μL) and R2 (40 μL) containing different amounts of the substrate. Substrate hydrolysis was immediately monitored at room temperature for 10 minutes. Lower substrate concentrations indicate greater drug inhibition. Activity values approached the lower limit of quantitation at the higher drug levels when the substrate was used at 154 μM or less due to slower hydrolysis rates. Consequently, the substrate concentration should be maintained slightly above its Km in order to drive rapid substrate hydrolysis while maintaining drug inhibition levels, as shown in Table 13.

TABLE 13

Effect of Substrate Concentration on Percent Inhibition of Lp-PLA2 Activity

| | Substrate Concentration (uM) | | | |
|---|---|---|---|---|
| Drug (ng/mL) | 275 | 550 | 1100 | 2200 |
| 0 | 0.00 | 0.00 | 0.00 | 0.00 |
| 2 | 32.43 | 26.84 | 18.32 | 17.33 |
| 5 | 31.02 | 34.92 | 16.53 | 30.96 |

TABLE 13-continued

Effect of Substrate Concentration on Percent Inhibition of Lp-PLA2 Activity

| Drug (ng/mL) | Substrate Concentration (uM) | | | |
|---|---|---|---|---|
| | 275 | 550 | 1100 | 2200 |
| 10 | 51.38 | 50.23 | 25.26 | 42.68 |
| 30 | 67.57 | 56.99 | 46.00 | 28.30 |
| 60 | 76.88 | 72.98 | 59.86 | 52.77 |
| 90 | 86.12 | 81.83 | 71.89 | 70.69 |

Example 16

Effect of Human Plasma Sample Volume on Drug-Sensitivity

Two μL of plasma were assayed in a 320 μL reaction for the Auto PAF AH assay, which corresponds to a plasma dilution factor of 160-fold. High plasma dilution may promote drug dissociation from Lp-PLA2. Consequently, 5 to 50 μL of an in vitro Lp-PLA2 inhibitor Formula II treated plasma sample were diluted with varying volumes of R1 and 40 μL of R2 to a final volume of 165 μL containing 1100 μM substrate. Hydrolysis was immediately monitored at room temperature for 10 minutes. Greater drug inhibition was observed with higher plasma sample volumes, as shown in Table 14.

TABLE 14

Effect of Sample Volume on Percent Inhibition of Lp-PLA2 activity

| Drug (ng/mL) | Plasma Sample Volume (μL) | | | |
|---|---|---|---|---|
| | 5 | 15 | 25 | 50 |
| 0 | 0.00 | 0.00 | 0.00 | 0.00 |
| 2 | 88.47 | 4.15 | 18.32 | 13.22 |
| 5 | 09.11 | 19.85 | 16.53 | 10.26 |
| 10 | −14.73 | 39.11 | 25.26 | 33.03 |
| 30 | 33.90 | 23.53 | 46.00 | 55.58 |
| 60 | 34.14 | 56.68 | 59.86 | 67.68 |
| 90 | 43.78 | 62.68 | 71.89 | 79.14 |

Example 17

Effect of Deletion of Buffer 2A on Drug-Sensitivity

In the Auto PAF AH assay, the substrate stock solution R2B is premixed in buffer R2A (20 mM citric acid monohydrate, 10 mM sodium 1-nonanesulfonate, pH 4.5), which acts as a substrate stabilizer. The substrate, after diluted in R2A, remains stable at 4° C. for 14 days. Faster hydrolysis rate was observed when R2A was omitted from the assay. For example, a colorimetric assay was performed with nmol of substrate (2 μL of R2B) and either 25 μL or 50 μL of plasma. Additionally, samples contained either 0 μL or 40 μL of R2A. All reactions were diluted to either 125 μl or 165 μL with R1. Buffer components were pre-mixed and the reaction was initiated upon human plasma addition. Substrate hydrolysis was immediately monitored at room temperature for 10 minutes. Vmax (milliOD/min) was calculated and compared among different conditions. Higher hydrolysis rates were observed upon omission of R2A, independent of plasma volume as shown in Table 15.

TABLE 15

Effect of the Deletion of Buffer R2A from the Assay

| | Sample | | | | | |
|---|---|---|---|---|---|---|
| | 1 | 2 | 3 | 4 | 5 | 6 |
| R1 | 100 μL | 140 μL | 100 μL | 75 μL | 115 μL | 75 μL |
| R2A | 40 μL | 0 μL | 0 μL | 140 μL | 0 μL | 0 μL |
| R2B | 2 μL | 2 μL | 2 μL | 2 μL | 2 μL | 2 μL |
| Plasma | 25 μL | 25 μL | 25 μL | 50 μL | 50 μL | 50 μL |
| Vmax (milliOD/Minute) | 40 | 90 | 70 | 40 | 150 | 120 |

Since R2A has low pH of 4.5 compared with the other assay buffer components, whether addition of R2A affected the pH of the assay reaction was determined. The pH of assay reactions containing 110 μL of R1, 0.66 μL of R2B and 25 μL of either plasma or ddH$_2$O were 7.52 and 7.53, respectively. The pH dropped to 7.43 and 7.42, respectively, when 40 μL of R2A were added to these assay samples. The effect of R2A on Lp-PLA2 hydrolysis rates of the substrate is probably more than pH-related.

Elimination of R2A from the assay increased hydrolysis rates, thereby allowing the use of lower substrate concentrations and shorter assay incubation times, both of which lower drug dissociation. Lp-PLA2 activity values approached the lower limit of quantitation when 25 μL of plasma were measured using 154 μM of substrate and R2A as described in Example 14. A substrate titration experiment was repeated using 50 μL of in vitro Formula II-treated plasma (subject #10) and 75 μL of assay buffer containing only R1 and R2B (no R2A). Assays were monitored at room temperature for 10 minutes at 405 nm and Vmax and drug inhibition were calculated. Hydrolysis activity exceeded the lower limit of quantitation at 900 and 9000 ng/mL of drug even at substrate concentrations as low as 65 μM (see Table 16). Consequently, R2A was eliminated and lower substrate concentrations were incorporated in a modified colorimetric activity assay.

TABLE 16

Effect of Substrate Concentration on Vmax of Substrate Hydrolysis
Vmax (milliOD/min) of Substrate Hydrolysis in Absence of Buffer R2A

| Drug (ng/mL) | Substrate Concentration (uM) | | | | | |
|---|---|---|---|---|---|---|
| | 273 | 205 | 154 | 115 | 86 | 65 |
| 9000 | 10.18 | 13.01 | 5.70 | 5.76 | 5.23 | 3.40 |
| 900 | 14.25 | 10.45 | 6.66 | 5.32 | 4.54 | 4.06 |
| 90 | 98.56 | 72.58 | 64.27 | 61.08 | 53.56 | 44.88 |
| 30 | 117.89 | 94.33 | 83.66 | 75.21 | 65.47 | 54.08 |
| 10 | 114.89 | 93.75 | 79.87 | 76.21 | 67.31 | 54.90 |

TABLE 16-continued

Effect of Substrate Concentration on
Vmax of Substrate Hydrolysis
Vmax (milliOD/min) of Substrate Hydrolysis
in Absence of Buffer R2A

| Drug | Substrate Concentration (uM) | | | | | |
|---|---|---|---|---|---|---|
| (ng/mL) | 273 | 205 | 154 | 115 | 86 | 65 |
| 5 | 112.58 | 93.22 | 82.11 | 76.71 | 66.46 | 52.99 |
| 0 | 110.82 | 90.18 | 80.40 | 73.58 | 63.73 | 56.30 |

Earlier studies indicated higher drug inhibition as the substrate concentration was lowered over 2200 μM to 273 μM in combination with 25 uL of human plasma. However, no significant effect on drug inhibition was observed when substrate concentration was lowered over 273 μM to 65 μM using 50 μL of plasma, which suggests drug dissociation is not promoted by lower substrate levels with higher plasma volumes over this range.

Example 18

Design of Experiment Software

After identifying individual factors that contribute to the drug insensitivity of the original Auto PAF AH assay, JMP software (Design of Experiment, herein "DOE") was used to design experiments investigating interactions between individual factors and to identify optimal combinations for detecting drug inhibition over an adequate dynamic range.

DOE Experiment #1

The first DOE experiment focused on four factors including buffer R1 volume (2 levels), plasma volume (4 levels), substrate concentration (8 levels) and drug treatment (2 levels). [The indicated levels of substrate concentration refer to the substrate concentration in the aliquot of premixed R2B/R1 added to each reaction unless otherwise noted.] Although a full factorial combination of variables would require 128 assay reactions, D-optimal design suggested 48 different combinations. These 48 reactions were performed in duplicate, using a single plasma sample with or without prior in vitro incubation with Formula II at 37° C. for an hour. Substrate was directly diluted into R1 and plasma was then added to start hydrolysis at room temperature. Vmax and drug inhibition were calculated based on absorbance readings at 405 nm over 5 minutes at room temperature.

JMP predicted that a combination of 15 μL or 25 μL of plasma and 110 μL of R1 containing 273 μM to 1100 μM substrate would indicate 90% or greater drug inhibition. This set of conditions would also yield reasonably high Vmax so that heavily drug-treated plasma would not fall below the lower limit of quantitation. The lowest substrate concentration included in this experiment, 65 μM in 110 μL of R1, was predicted to detect 93.41% drug inhibition when used with 25 μL of plasma (final substrate concentration of 53 uM). However, Vmax prediction was as low as 16.79 for the non-drug-treated sample. Such condition, although did not proceed for further optimization, could be used to assay specific sample sets that have low and narrow range of Lp-PLA2 activity.

DOE Experiment #2

The second DOE experiment focused on the conditions identified by the prior DOE experiment. It designed a full factorial combination of all variables including R1 volume (1 level), plasma volume (2 levels), substrate concentration (4 levels) and drug treatment (4 levels). Thirty-two conditions were assayed in duplicate. The assay protocol was identical to the first DOE experiment. [The indicated levels of substrate concentration again refer to the substrate concentration in the aliquot of premixed R2B/R1 added to each reaction unless otherwise noted.] Prediction Profiler predicted that 25 μL plasma and 110 μL of R1 containing 545 μM substrate would generate a Vmax of 76 milliOD/min for non-drug treated plasma and indicate close to 95% drug inhibition for plasma treated with 900 ng/mL of drug in vitro. Therefore, a modified, drug-sensitive assay uses 25 μL of plasma with 110 μL of R1 containing 545 μM substrate for a final substrate concentration of 440 μM in the assay.

An alternative set of conditions was also identified (15 μL of plasma and 110 μL of R1 containing 545 μM for a final substrate concentration of 475 μM in the assay) that indicated 94% drug inhibition and Vmax=53 milliOD/min for non-drug-treated plasma.

Example 19

Reaction Time

Four human plasma timepoint samples from a single subject, who was treated in vivo with Lp-PLA2 inhibitor drug, were assayed for Lp-PLA2 activity by a modified, drug-sensitive colorimetric assay containing 440 μM substrate and 25 μL of plasma (described in Example 8). The same four plasma samples were also assayed by the same assay protocol but with 50 μL of plasma and 154 μM of substrate (see Table 17). The first 5 minutes of hydrolysis were monitored for each reaction and five Vmax values were calculated based on time intervals of 1, 2, 3, 4 or 5 minutes from the start of the reaction. Samples corresponding to high Lp-PLA2 inhibition (1 and 3 hour post-dose) exhibited higher Vmax values for longer assay reaction times when 25 μL plasma and 440 μM substrate were used. This suggests drug dissociation may occur under such condition where competition between drug and substrate is relatively strong. In contrast, Vmax values for 1 and 3 hour post-dose time points were independent of assay reaction time when more plasma and lower substrate was used (e.g., 50 μL plasma/154 M substrate). However, Vmax values tend to decrease with longer assay reaction times for samples with lower drug inhibition (0 and 0.5 hours) especially at higher plasma volume and lower substrate concentration as appreciable total substrate is consumed with high Lp-PLA2 activity. Therefore, assay performance is affected by at least three factors affecting three attributes:

(1) High plasma volume, short incubation time and low substrate concentration promote measurement of high levels of drug inhibition;
(2) Low plasma volume, short incubation time and high substrate concentration promote a high upper limit of quantitation;
(3) High plasma volume, long incubation time and high substrate concentration promote sensitive lower limits of quantitation.

The implementation of robotics is recommended to shorten the time between addition of substrate into plasma and the first absorbance reading on the plate reader. Current protocol assembles and mixes an entire microtiter plate of reactions and start plate reading 1 minute after starting the first reaction on the plate. Activity calculations are based on data collected at 1 and 3 minutes in the microtiter plate reader. However, since absorbance readings are collected for 10 minutes at 15-second intervals, depending on the objective of the assay and range of activity seen with a specific sample set, shorter and/or earlier, or longer reaction time could be chosen to calculate Lp-PLA2 activity.

TABLE 17

Effect of Reaction Time on Reaction Rate Under Different Plasma Volume and Substrate Concentrations

| Time | Vmax (milliOD/min) | | | | | | | | | |
|---|---|---|---|---|---|---|---|---|---|---|
| | 25 μL Plasma/440 μM Substrate | | | | | 50 μL Plasma/154 μM Substrate | | | | |
| (Hr) | 1 min | 2 min | 3 min | 4 min | 5 min | 1 min | 2 min | 3 min | 4 min | 5 min |
| 0 | 125.20 | 118.65 | 115.01 | 110.60 | 107.85 | 98.70 | 88.45 | 82.73 | 76.54 | 70.68 |
| 0.5 | 86.90 | 88.70 | 88.73 | 88.79 | 88.38 | 76.50 | 72.85 | 69.05 | 64.78 | 61.71 |
| 1 | 19.00 | 21.05 | 23.37 | 25.72 | 27.90 | 18.00 | 17.75 | 18.01 | 18.10 | 18.28 |
| 3 | 6.30 | 8.25 | 10.65 | 12.74 | 14.70 | 10.20 | 9.15 | 9.24 | 9.37 | 9.57 |

Example 20

Further Assay Testing

Inter-Assay Validation

Intra-assay variability was assessed using plasma samples from 10 healthy (non-fasted) human subjects. Six replicates of plasma from each subject were assayed on the same assay plate. The CV for individual subjects ranged from 2.57 to 9.14% with an average intra-assay CV of 5.36% as shown in Table 18.

TABLE 18

Intra-Assay Validation
Lp-PLA2 Activity (nmol/min/mL)

| Replicate | Subject No. | | | | | | | | | |
|---|---|---|---|---|---|---|---|---|---|---|
| No. | #6954966 | #5149192 | #6839829 | #5147931 | #5181480 | #5149190 | #5149188 | #6954955 | #6955001 | #6716001 |
| 1 | 112.26 | 64.53 | 147.94 | 138.05 | 94.56 | 105.37 | 132.26 | 140.35 | 140.56 | 139.30 |
| 2 | 115.68 | 78.40 | 137.14 | 135.75 | 93.59 | 97.35 | 109.41 | 135.33 | 124.53 | 145.92 |
| 3 | 108.92 | 74.29 | 156.52 | 146.62 | 90.45 | 113.87 | 111.78 | 129.55 | 119.30 | 145.30 |
| 4 | 113.24 | 74.49 | 174.22 | 143.55 | 93.10 | 102.86 | 107.25 | 138.82 | 116.93 | 140.14 |
| 5 | 108.01 | 69.62 | 138.47 | 140.28 | 92.82 | 120.07 | 107.87 | 128.85 | 130.31 | 140.14 |
| 6 | 113.31 | 80.14 | 146.83 | 145.16 | 91.85 | 114.70 | 112.89 | 134.70 | 136.59 | 147.87 |
| Average | 111.90 | 73.58 | 150.19 | 141.57 | 92.73 | 109.04 | 113.58 | 134.60 | 128.04 | 143.11 |
| % CV | 2.60 | 7.81 | 9.14 | 3.00 | 1.54 | 7.84 | 8.29 | 3.48 | 7.38 | 2.57 |

Inter-Assay Variability

Inter-assay variability was assessed using plasma samples from 10 healthy human subjects (non-fasted), assayed in three separate assays on different days. The inter-assay CV for individual plasma samples ranged from 1.90 to 23.78% with an average inter-assay CV of 7.59%. Plasma from Subject #5181480 (inter-assay CV=23.78%) had a white/turbid appearance after brief centrifugation, suggesting high lipid content in the sample as shown in Table 19.

TABLE 19

Inter-Assay Variability
Lp-PLA2 Activity (nmol/min/mL)

| Assay | Subject No. | | | | | | | | | |
|---|---|---|---|---|---|---|---|---|---|---|
| No. | #6954966 | #5149192 | #6839829 | #5147931 | #5181480 | #5149190 | #5149188 | #6954955 | #6955001 | #6716001 |
| 1 | 111.90 | 73.58 | 150.19 | 141.57 | 92.73 | 109.04 | 113.58 | 134.60 | 128.04 | 143.11 |
| 2 | 105.75 | 76.77 | 143.36 | 127.71 | 58.21 | 106.36 | 112.86 | 106.26 | 116.87 | 134.58 |
| 3 | 117.70 | 83.78 | 147.66 | 118.56 | 70.17 | 97.80 | 116.94 | 120.69 | 130.48 | 134.02 |
| Average | 111.79 | 78.04 | 147.07 | 129.28 | 73.70 | 104.40 | 114.46 | 120.52 | 125.13 | 137.24 |
| % CV | 5.34 | 6.69 | 2.35 | 8.96 | 23.78 | 5.62 | 1.90 | 11.76 | 5.80 | 3.71 |

Inter-Operator Variability

Inter-operator variability was assessed using plasma samples from 10 healthy subjects assayed by three different operators on different days. The inter-operator CV for individual plasma samples ranged from 5.11 to 14.91% with an average inter-operator CV of 8.32% as shown in Table 20.

TABLE 20

Inter-Operator Variability
Lp-PLA2 Activity (nmol/min/mL)

| Operator No. | Subject No. | | | | | | | | | |
|---|---|---|---|---|---|---|---|---|---|---|
| | #6954966 | #5149192 | #6839829 | #5147931 | #5181480 | #5149190 | #5149188 | #6954955 | #6955001 | #6716001 |
| 1 | 111.79 | 78.04 | 147.07 | 129.28 | 73.70 | 104.40 | 114.46 | 120.52 | 125.13 | 137.24 |
| 2 | 107.20 | 70.46 | 128.55 | 128.06 | 66.74 | 100.98 | 106.22 | 114.00 | 114.09 | 109.69 |
| 3 | 98.60 | 74.85 | 136.87 | 111.37 | 62.05 | 82.44 | 102.25 | 100.23 | 112.41 | 104.82 |
| Average | 105.86 | 74.45 | 137.50 | 122.90 | 67.50 | 95.94 | 107.64 | 111.58 | 117.21 | 117.25 |
| % CV | 6.32 | 5.11 | 6.75 | 8.14 | 8.69 | 12.31 | 5.79 | 9.28 | 5.89 | 14.91 |

Freeze/Thaw Effect

Plasma samples are normally received and stored frozen. In the case of repeat analysis, samples are commonly subject to freeze/thaw cycles. Ten plasma samples were analyzed after each of four freeze/thaw cycles. No definitive trend in Lp-PLA2 values was observed, indicating samples may be frozen and thawed four times, a shown in Table 20.

TABLE 21

Freeze/Thaw Effect
Lp-PLA2 Activity (nmol/min/mL)

| Freeze/Thaw | Subject No. | | | | | | | | | |
|---|---|---|---|---|---|---|---|---|---|---|
| | 6954966 | 5149192 | 6839829 | 5147931 | 5181480 | 5149190 | 5149188 | 6954955 | 6955001 | 6716001 |
| 1 | 111.90 | 73.58 | 150.19 | 141.57 | 92.73 | 109.04 | 113.58 | 134.60 | 128.04 | 143.11 |
| 2 | 105.75 | 76.77 | 143.36 | 127.71 | 58.21 | 106.36 | 112.86 | 106.26 | 116.87 | 134.58 |
| 3 | 112.72 | 82.20 | 141.72 | 107.84 | 53.78 | 81.48 | 116.70 | 99.18 | 130.55 | 125.98 |
| 4 | 101.09 | 68.94 | 105.00 | 95.96 | 55.96 | 97.12 | 98.05 | 122.05 | 105.40 | 169.87 |
| Average | 107.87 | 75.37 | 135.07 | 118.27 | 65.17 | 98.50 | 110.30 | 115.52 | 120.21 | 143.38 |
| % CV | 5.08 | 7.39 | 15.09 | 17.18 | 28.33 | 12.63 | 7.56 | 13.77 | 9.59 | 13.24 |

Example 21

Higher Drug Inhibition and Assay Dynamic Range

Four hundred forty microMolar (440 µM) substrate and 25 µL of plasma sample volume were selected for use in the current modified assay protocol since they offered high detectable in vivo drug inhibition while maintaining adequate assay dynamic range. However, further lowering substrate concentration and/or increasing plasma sample volume in the assay could detect higher measurable drug inhibition in vivo at expense of assay dynamic range. Plasma samples from 5 human subjects receiving Formula II for 9 days in a clinical study were collected on day 10 at different time points. Pre-dose plasma samples for each subject on day 0 of the study were also available. When 440 µM substrate and 25 µL of plasma were used in the assay, maximal 68% drug inhibition was observed in Subject N030 at 4 hour-timepoint as shown in Table 22. Lowering substrate concentration to 112 µM while maintaining 25 µL of plasma volume increased drug inhibition to 76% at this time point. Further increase in drug inhibition to 79% at 4 hour-timepoint, was achieved with both lower substrate concentration of 112 µM and higher plasma volume of 45 µL.

TABLE 22

Improved Detectable Inhibition in Human Subjects Administered
Lp-PLA2 Inhibitor

| | Lp-PLA activity (nmol/min/mL) | | | % Inhibition | | |
|---|---|---|---|---|---|---|
| Time (hr) | 440 µM/25 µL | 112 µM/25 µL | 112 µM/45 µL | 440 µM/25 µL | 112 µM/25 µL | 112 µM/45 µL |
| Pre-dose | 110.59 | 38.95 | 35.59 | 0 | 0 | 0 |
| 0 | 51.85 | 14.41 | 11.58 | 53 | 63 | 67 |
| 0.5 | 48.74 | 15.08 | 8.87 | 56 | 61 | 75 |
| 1 | 47.39 | 12.10 | 9.55 | 57 | 69 | 73 |
| 2 | 41.97 | 14.54 | 11.48 | 62 | 63 | 68 |

TABLE 22-continued

Improved Detectable Inhibition in Human Subjects Administered Lp-PLA2 Inhibitor

| Time (hr) | Lp-PLA activity (nmol/min/mL) | | | % Inhibition | | |
|---|---|---|---|---|---|---|
| | 440 µM/25 µL | 112 µM/25 µL | 112 µM/45 µL | 440 µM/25 µL | 112 µM/25 µL | 112 µM/45 µL |
| 3 | 40.67 | 11.51 | 6.54 | 63 | 70 | 82 |
| 4 | 35.88 | 9.37 | 7.31 | 68 | 76 | 79 |
| 6 | 43.32 | 9.62 | 6.12 | 61 | 75 | 83 |
| 9 | 39.37 | 10.59 | 7.52 | 64 | 73 | 79 |
| 12 | 39.66 | 11.22 | 8.85 | 64 | 71 | 75 |
| 18 | 48.87 | 13.53 | 11.32 | 56 | 65 | 68 |
| 24 | 39.08 | 8.24 | 6.30 | 65 | 79 | 82 |

Plasma samples from the other four subjects were analyzed using both 440 µM substrate/25 µL plasma and 112 µM substrate/45 µL plasma assay condition. The maximal drug inhibition detected with 440 µM substrate and 25 µL plasma was between 68% and 80% in these subjects as shown in Table 23. However, the use of 112 µM substrate and 45 µL of plasma further improved measurable drug inhibition in the same subjects with maximal inhibition between 87% and 98%. With 112 µM substrate/45 µL plasma, the absolute Lp-PLA2 activity value decreased significantly with those at highest drug inhibition points approaching lower limit of p-nitrophenol linear detection range described in Example 12. For example, the 4 hour-timepoint plasma for Subject N028 showed Lp-PLA activity of 1.31 nmol/min/mL (see Table 23). Such level of activity would only generate 0.12 nmol of p-nitrophenol in two minutes of assay time based on a modified drug sensitive colorimetric assay described in Example 8, slightly above the low end of p-nitrophenol linear detection range 0.1 nmol.

TABLE 23

Improved Detectable Inhibition

| Subject No. | Time (hr) | Lp-PLA2 Activity (nmol/min/mL) | | % Inhibition | |
|---|---|---|---|---|---|
| | | 440 µM/25 µL | 112 µM/45 µL | 440 µM/25 µL | 112 µM/45 µL |
| N008 | Pre-dose | 104.20 | 25.81 | 0 | 0 |
| | 0 | 47.06 | 12.65 | 55 | 51 |
| | 0.5 | 45.87 | 12.67 | 47 | 51 |
| | 1 | 53.40 | 11.37 | 49 | 56 |
| | 2 | 61.13 | 13.14 | 41 | 49 |
| | 3 | 52.48 | 13.42 | 50 | 48 |
| | 4 | 46.51 | 6.19 | 55 | 76 |
| | 6 | 33.95 | 3.27 | 67 | 87 |
| | 9 | 43.87 | 6.21 | 58 | 76 |
| | 12 | 33.66 | 5.74 | 68 | 78 |
| | 18 | 62.77 | 6.54 | 40 | 75 |
| | 24 | 65.38 | 11.16 | 37 | 57 |
| N009 | Pre-dose | 168.28 | 42.62 | 0 | 0 |
| | 0 | 69.03 | 14.49 | 59 | 66 |
| | 0.5 | 66.97 | 16.97 | 60 | 60 |
| | 1 | 69.71 | 19.42 | 59 | 54 |
| | 2 | 73.99 | 17.16 | 56 | 60 |
| | 3 | 68.87 | 13.12 | 59 | 69 |
| | 4 | 54.75 | 3.64 | 67 | 91 |
| | 6 | 53.19 | 10.97 | 68 | 74 |
| | 9 | 60.76 | 11.27 | 64 | 74 |
| | 12 | 76.09 | 12.58 | 55 | 70 |
| | 18 | 71.39 | 18.51 | 58 | 57 |
| | 24 | 69.12 | 16.69 | 59 | 61 |
| N028 | Pre-dose | 188.82 | 53.36 | 0 | 0 |
| | 0 | 60.50 | 7.80 | 68 | 85 |
| | 0.5 | 54.96 | 3.29 | 71 | 94 |
| | 1 | 53.70 | 6.28 | 72 | 88 |
| | 2 | 62.98 | 7.24 | 67 | 86 |
| | 3 | 64.87 | 4.06 | 66 | 92 |
| | 4 | 42.65 | 1.31 | 77 | 98 |
| | 6 | 37.35 | 3.55 | 80 | 93 |
| | 9 | 43.99 | 2.99 | 77 | 94 |
| | 12 | 45.88 | 5.30 | 76 | 90 |
| | 18 | 53.56 | 13.40 | 72 | 75 |
| | 24 | 56.68 | 11.69 | 70 | 78 |
| N029 | Pre-dose | 139.03 | 73.80 | 0 | 0 |
| | 0 | 70.50 | 16.59 | 49 | 78 |
| | 0.5 | 65.92 | 15.45 | 53 | 79 |
| | 1 | 73.03 | 16.76 | 47 | 77 |
| | 2 | 62.98 | 15.33 | 55 | 79 |
| | 3 | 46.81 | 5.88 | 66 | 92 |

TABLE 23-continued

Improved Detectable Inhibition

| Subject No. | Time (hr) | Lp-PLA2 Activity (nmol/min/mL) | | % Inhibition | |
|---|---|---|---|---|---|
| | | 440 μM/25 μL | 112 μM/45 μL | 440 μM/25 μL | 112 μM/45 μL |
| | 4 | 46.09 | 5.39 | 67 | 83 |
| | 6 | 41.09 | 4.11 | 70 | 94 |
| | 9 | 44.12 | 6.54 | 68 | 91 |
| | 12 | 50.13 | 8.64 | 64 | 88 |
| | 18 | 59.08 | 10.71 | 58 | 85 |
| | 24 | 62.56 | 19.75 | 55 | 73 |

To define the assay dynamic range for using 112 μM of substrate and 45 μL of plasma, serially diluted recombinant human Lp-PLA2 protein was assayed for Lp-PLA2 activity. The activity of hrLp-PLA2 between 4.88 to 312.50 ng/mL demonstrated linearity with an R value of 0.96 (see Table 24). Therefore, the dynamic range appears to be between 2.71 and 84.14 nmol/min/mL. Compared to the dynamic range between 4.4 and 397 nmol/min/mL for 440 μM of substrate and 25 μL of plasma determined in Example 12 using hrLp-PLA, 112 μM substrate/45 μL plasma, although lowering low limit of quantitation, could only offer limited assay range. Therefore, such conditions with lower substrate concentration and higher sample volume could be used when higher measurable in vivo inhibition is desired while the range of Lp-PLA2 activity for test samples is limited or could be compromised. One example such conditions could be applied to is in clinical studies for Lp-PLA2 inhibitor drugs in which most post-drug test samples demonstrate low Lp-PLA2 activity resulted from drug inhibition. Earlier and shorter reaction time could be considered to use in activity calculation to improve assay dynamic range when such conditions are used.

TABLE 24

Assay of Recombinant Human Lp-PLA2 Using 112 μM Substrate/45 μL Plasma

| hrLp-PLA2 (ng/mL) | Activity (nmol/min/mL) |
|---|---|
| 0.00 | 0.00 |
| 1.22 | 0.18 |
| 2.44 | 0.62 |
| 4.88 | 2.71 |
| 9.77 | 5.13 |
| 19.53 | 9.27 |
| 39.06 | 17.81 |
| 78.13 | 30.16 |
| 156.25 | 51.62 |
| 312.50 | 84.14 |
| 625.00 | 109.44 |
| 1250.00 | 93.90 |

The assay dynamic range of 2.71-84.14 nmol/min/mL determined by hrLp-PLA2 was calculated based on absorbance change between 3 minutes and 1 minute after the start of reaction. When absorbance differences between 1 minute and 0 minutes of the reaction were used to calculate Lp-PLA2 activity from the same data, dynamic range was significantly improved to 3.2-196.5 nmol/min/mL (see Table 25). Shortening reaction time to 30 seconds in activity calculation showed little further improvement.

TABLE 25

Effect of Reaction Time Used for Activity Calculation on Assay Dynamic Range

| Reaction Time Used for Activity Calculation | hrLp-PLA2 (ng/ml) | Activity (nmol/min/mL) | R |
|---|---|---|---|
| 3 min-1 min | 14.6-938 | 2.71-84.1 | 0.98 |
| 1 min-0 | 14.6-3750 | 3.2-196.5 | 0.97 |
| 30 sec-0 | 14.6-3750 | 3.4-210 | 0.98 |

Example 22

Detection of Lp-PLA2 Activity and its In Vitro Drug Inhibition in Serum

To assess the utility of a modified colorimetric assay for measuring Lp-PLA2 activity and particularly its drug inhibition in serum, 10 serum samples collected from normal donors were assayed. The measured Lp-PLA2 activity shown in Table 26 ranged between 130 and 190 nmol/min/mL for these serum samples. The % CV between duplicates of each sample was mostly less than 5%. No matched plasma samples were available for analysis. However, pre-dose plasma samples from 14 subjects described in Example 10 and 11 showed a comparable range of Lp-PLA2 activity between 80 and 200 nmol/min/mL.

TABLE 26

Lp-PLA2 Activity in Ten Serum Samples

| Sample | Activity (nmol/min/mL) | % Inhibition |
|---|---|---|
| BRH28858 | 145.57 | 5.28 |
| BRH28859 | 131.36 | 1.73 |
| BRH28860 | 177.74 | 0.75 |
| BRH28861 | 187.11 | 0.79 |
| BRH28862 | 155.68 | 1.65 |
| BRH28865 | 144.04 | 3.28 |
| BRH28866 | 133.28 | 1.52 |
| BRH28867 | 131.28 | 2.92 |
| BRH28868 | 137.35 | 1.15 |
| BRH28869 | 140.00 | 3.66 |

Since no serum samples were available from human subjects administered Lp-PLA2 inhibitors, 2 serum samples, BRH28861 and BRH28867, were pre-treated in vitro with different doses of Lp-PLA2 inhibitor Formula II. The dose range used in vitro contained the range of in vivo plasma concentrations of such inhibitor in human subjects receiving drug during clinical studies of Formula II. Based on pharmacokinetics data, 90 ng/mL represented the peak plasma level of Formula II when administered in vivo. These in vitro drug-treated serum samples were then assayed for Lp-PLA2 activity by a modified colorimetric assay. Table 27 showed that BRH28861 and BRH28867 reached 88.25% and 90.77% inhibition of Lp-PLA2 activity, respectively, when treated with 90 ng/mL of Formula II in vitro. Higher drug dose at 900 ng/mL level further increased drug inhibition to 97.71% and 92.28% respectively in these two serum samples.

TABLE 27

In vitro Drug Inhibition of Serum Lp-PLA2 Activity

| Drug | Activity (nmol/min/mL) | | % Inhibition | |
| --- | --- | --- | --- | --- |
| (ng/mL) | BRH28861 | BRH28867 | BRH28861 | BRH28867 |
| 0 | 153.90 | 110.17 | 0.00 | 0.00 |
| 1 | 166.90 | 103.62 | −8.44 | 5.95 |
| 2 | 137.46 | 92.54 | 10.69 | 16.00 |
| 5 | 154.60 | 103.66 | −0.45 | 5.91 |
| 10 | 137.70 | 82.47 | 10.53 | 25.14 |
| 30 | 55.54 | 40.38 | 63.91 | 63.35 |
| 60 | 16.34 | 13.66 | 89.38 | 87.60 |
| 90 | 18.08 | 10.17 | 88.25 | 90.77 |
| 900 | 3.52 | 7.91 | 97.71 | 92.82 |

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

What is claimed is:

1. A method for determining inhibition of Lp-PLA2 enzyme activity in at least one sample comprising the steps of:
    (a) preparing a solution comprising a substrate for lipoprotein-associated phospholipase A2 ("Lp-PLA2") comprising a colorimetric or fluorometric detectable moiety;
    (b) contacting at least one said sample with the solution of step (a); and
    (c) detecting Lp-PLA2 activity;
wherein the sample is from an animal that has been administered an Lp-PLA2 inhibitor and wherein the sample is diluted about 3 to about 9 fold by contact with the solution of step (a).

2. The method of claim 1, further comprising comparing Lp-PLA2 activity from at least one second sample obtained from an animal wherein said second sample is free of said Lp-PLA2 inhibitor.

3. The method of claim 1, wherein inhibition of Lp-PLA2 activity is determined in a plurality of samples obtained from an animal at more than one time point after administration of said Lp-PLA2 inhibitor.

4. The method of claim 1, wherein said substrate is 1-myristoyl-2-(4-nitrophenylsuccinyl) phosphatidylcholine.

5. The method of claim 4, wherein said substrate is used at a concentration of about 53 μM to about 1125 μM.

6. The method of claim 5, wherein said substrate is used at a concentration of about 440 μM or less.

7. The method of claim 5, wherein said substrate is used at a concentration of about 112 μM.

8. The method of claim 1, wherein the sample is blood plasma.

9. The method of claim 1, wherein the sample is serum.

10. The method of claim 1, wherein the Lp-PLA2 activity is detected by measuring optical density.

11. The method of claim 1, wherein the solution comprising a substrate for Lp-PLA2 further comprises a buffer and wherein the buffer is incubated with the substrate prior to contacting the substrate with said sample.

12. The method of claim 11, wherein the buffer does not comprise citric acid monohydrate.

13. The method of claim 1, wherein the substrate concentration is maintained at approximately the Km of said substrate.

14. The method of claim 1, wherein the volume of the sample is about 15 uL to about 50 μL in a volume of about 125 μL to about 170 μL of the solution of step (a).

15. The method of claim 1, wherein the pH of the reaction is maintained at at least about 7.5 prior to contacting the sample with the solution of step (a).

16. The method of claim 5, wherein said substrate is used at a concentration of about 1125 μM.

17. The method of claim 1, wherein the animal is human.

18. The method of claim 1, wherein the volume of the sample is about 15 μL to about 50 μL.

19. A method for determining Lp-PLA2 enzyme activity in a sample obtained from an animal that has been administered an Lp-PLA2 inhibitor comprising the steps of:
    a) contacting said sample with a solution comprising a substrate for Lp-PLA2 comprising a colorimetric or fluorometric detectable moiety; and
    b) detecting Lp-PLA2 activity;
wherein said sample is diluted about 3 to 9 fold by contact with the solution comprising a substrate.

20. The method of claim 19, wherein said sample is blood plasma or serum.

21. The method of claim 19, wherein said substrate is 1-myristoyl-2-(4-nitrophenylsuccinyl)phosphatidylcholine.

22. The method of claim 21, wherein said substrate is used at a concentration of about 53 uM to about 1125 uM.

23. The method of claim 21, wherein said substrate is used at a concentration of about 440 uM or less.

24. The method of claim 21, wherein said substrate is used at a concentration of about 1125 uM.

25. The method of claim 21, wherein said substrate is used at a concentration of about 112 uM.

26. The method of claim 19, wherein said substrate concentration is maintained at approximately the Km of said substrate.

27. The method of claim 19, wherein the Lp-PLA2 enzyme activity is detected by measuring optical density.

28. The method of claim 19, wherein the animal is human.

29. The method of claim 19, wherein Lp-PLA2 enzyme activity is determined in a plurality of samples obtained from an animal at more than one time point after administration of said Lp-PLA2 inhibitor.

30. The method of claim 19, wherein the volume of the sample is about 15 μL to about 50 μL.

31. A method for determining inhibition of Lp-PLA2 enzyme activity in at least one sample comprising the steps of:
    (a) preparing a solution comprising a substrate for lipoprotein-associated phospholipase A2 ("Lp-PLA2");
    (b) contacting at least one said sample with the solution of step (a); and
    (c) fluorometrically or colorimetrically detecting Lp-PLA2 activity;
wherein the sample is from an animal that has been administered an Lp-PLA2 inhibitor and wherein the sample is diluted about 3 to about 9 fold by contact with the solution of step (a).

32. The method of claim 31, wherein said substrate is 1-myristoryl-2-(4-nitrophenylsuccinyl) phosphatidylcholine.

33. The method of claim 31, wherein the sample is blood plasma or serum.

34. The method of claim 31, wherein the volume of the sample is about 15 uL to about 50 uL.

35. A method for determining Lp-PLA2 enzyme activity in a sample obtained from an animal that has been administered an Lp-PLA2 inhibitor comprising the steps of:
   a) contacting said sample with a solution comprising a substrate for Lp-PLA2; and
   b) fluorometrically or colorimetrically detecting Lp-PLA2 activity;

wherein said sample is diluted about 3 to 9 fold by contact with the solution comprising a substrate.

36. The method of claim 35, wherein said sample is blood plasma or serum.

37. The method of claim 35, wherein said substrate is 1-myristoryl-2-(4-nitrophenylsuccinyl) phosphatidylcholine.

38. The method of claim 35, wherein the volume of the sample is about 15 uL to about 50 uL.

* * * * *